(12) United States Patent
Shinoda et al.

(10) Patent No.: US 7,816,405 B2
(45) Date of Patent: Oct. 19, 2010

(54) CALCIUM BIS [(2S)-3-[3-[(2S)-3-(4-CHLORO-2-CYANOPHENOXY)-2-FLUOROPROPOXY]PHENYL ]-2-ISOPROPOXYPROPIONATE] AND INTERMEDIATE THEREOF

(75) Inventors: Masanobu Shinoda, Tsukuba (JP); Fumiyoshi Matsuura, Tsukuba (JP); Kaoru Murata, Tsukuba (JP); Masaharu Gotoda, Tsukuba (JP); Kenji Hayashi, Tsukuba (JP); Manabu Sasho, Tokyo (JP); Naoki Ozeki, Tsukuba (JP); Susumu Inoue, Hasaki-Machi (JP); Katsutoshi Nishiura, Hasaki-Machi (JP); Yoshihiko Hisatake, Hasaki-Machi (JP); Teiji Takigawa, Hasaki-Machi (JP); Mamoru Miyazawa, Hasaki-Machi (JP); Shigeto Negi, Hasaki-Machi (JP); Keisuke Matsuyama, Kobe (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 577 days.

(21) Appl. No.: 11/405,619

(22) Filed: Apr. 18, 2006

(65) Prior Publication Data
US 2007/0117866 A1 May 24, 2007

Related U.S. Application Data

(60) Provisional application No. 60/672,512, filed on Apr. 19, 2005.

(51) Int. Cl.
*A61K 31/277* (2006.01)
*C07C 255/55* (2006.01)
(52) U.S. Cl. .................... 514/521; 558/410
(58) Field of Classification Search ............ 514/521; 558/410
See application file for complete search history.

(56) References Cited

U.S. PATENT DOCUMENTS 4,895,873 A  1/1990 Schafer

| 7,056,942 B2 * | 6/2006 | Hildesheim et al. ......... 514/411 |
| 7,521,461 B2 * | 4/2009 | Li ............................... 514/307 |
| 2004/0102634 A1 * | 5/2004 | Matsuura et al. ............ 546/218 |

FOREIGN PATENT DOCUMENTS

| DE | 10020275 A1 | 10/2001 |
| EP | 0 271 586 A1 | 6/1988 |
| JP | 63-313746 A | 12/1988 |
| JP | 3-17054 A | 1/1991 |
| JP | 4-334339 A | 11/1992 |
| JP | 6-239788 A | 8/1994 |
| JP | 2000-281626 A | 10/2000 |
| JP | 2003-520835 A | 7/2003 |
| JP | 2004-18378 A | 1/2004 |
| JP | 2004-517891 A | 6/2004 |
| WO | WO-87/07603 A1 | 12/1987 |
| WO | WO-00/53566 A1 | 9/2000 |
| WO | WO-01/55078 A1 | 8/2001 |
| WO | WO-02/057251 A2 | 7/2002 |
| WO | WO 02/100812 A1 * | 12/2002 |
| WO | WO-02/100812 A1 | 12/2002 |
| WO | WO-03/106024 A1 | 12/2003 |

* cited by examiner

*Primary Examiner*—Joseph R Kosack
(74) *Attorney, Agent, or Firm*—Birch, Stewart, Kolasch & Birch, LLP

(57) ABSTRACT

The present invention relates to calcium bis[(2S)-3-[3-[(2S)-3-(4-chloro-2-cyanophenoxy) -2-fluoropropoxy]phenyl]-2-isopropoxypropionate] represented by formula (I), a hydrate thereof, a crystal of the compound of formula (I), and a crystal of the hydrate of the compound of formula (I) which are useful as pharmaceuticals, and to processes for producing the same, and intermediates therefore, and processes for production thereof.

There is need for (2S)-3-[3-[(2S)-3-(4 -chloro-2-cyanophenoxy)-2-fluoropropoxy]phenyl]-2-isopropoxypropionic acid, in the form of a drug substance, purified so as to minimize a residual solvent content and having a uniformized specification and a highly favorable workability, and a process for producing the same.

Crystalline calcium bis[(2S)-3-[3-[(2S)-3-(4 -chloro-2-cyanophenoxy)-2-fluoropropoxy]phenyl]-2-isopropoxypropionate], a calcium salt of (2S) -3-[3-[(2S)-3-(4-chloro-2-cyanophenoxy)-2-fluoropropoxy]phenyl]-2-isopropoxypropionic acid, solves the above problem.

4 Claims, 1 Drawing Sheet

CALCIUM BIS [(2S)-3-[3-[(2S)-3-(4-CHLORO-2-CYANOPHENOXY)-2-FLUOROPROPOXY]PHENYL ]-2-ISOPROPOXYPROPIONATE] AND INTERMEDIATE THEREOF

TECHNICAL FIELD

The present invention relates to calcium bis[(2S)-3-[3-[(2S)-3-(4-chloro-2-cyanophenoxy)-2-fluoropropoxy]phenyl]-2-isopropoxypropionate] represented by formula (I):

[Formula 1]

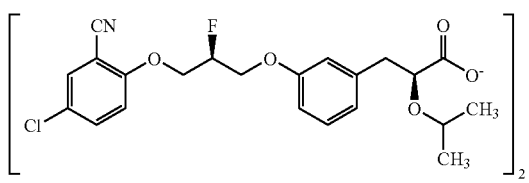

a hydrate thereof, a crystal of the compound of formula (I), and a crystal of the hydrate of the compound of formula (I) which are useful as pharmaceuticals, and to processes for producing the same and intermediates therefor and processes for production thereof.

BACKGROUND ART

The compound of formula (I), the hydrate thereof, the crystal of the compound of formula (I), and the crystal of the hydrate of the compound of formula (I) are novel compounds, and the processes for producing these compounds are therefore novel producing processes. A compound represented by formula (V):

[Formula 2]

(V)

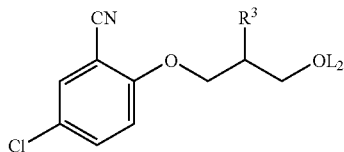

(wherein $R^3$ represents

[Formula 3]

$\underset{\vdots}{\overset{\vdots}{O}H}$ or $\underset{\blacktriangledown}{F}$ and $L_2$ represents a hydrogen atom or a protecting group for a hydroxyl group) and a compound represented by formula (VI):

[Formula 4]

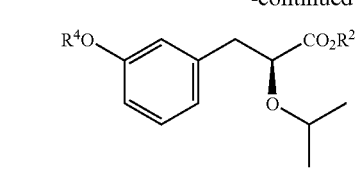

(VI)

(wherein $R^2$ represents a hydrogen atom or a protecting group for a carboxyl group and $R^4$ represents a hydrogen atom or a protecting group for a hydroxyl group), or salts thereof, which are important intermediates for the above-described compounds, are novel compounds, and processes for production the same are therefore novel producing processes.

A compound of formula (II) which is a precursor for the compound of formula (I) is a well-known compound, and known to be useful as an insulin sensitizing agent, a prophylactic or therapeutic agent against diabetes, a prophylactic or therapeutic agent against syndrome X, a prophylactic or therapeutic agent against diabetic complications, a prophylactic or therapeutic agent against hyperlipemia, a hypolipidemic agent, a prophylactic or therapeutic agent against obesity, an osteoporosis-treating agent, an anti-inflammatory agent, or a prophylactic or therapeutic agent against digestive system diseases (see, for example, Patent Reference 1).

[Patent Reference 1] WO02/100812

The compound of formula (II) corresponds to a compound described in Example 329 of WO02/100812, but the patent document does not directly disclose the compound of formula (I), which comprises two molecules of the compound of formula (II) and a calcium element, a hydrate thereof, a crystal of the compound of formula (I), and a crystal of the hydrate of the compound of formula (I).

DISCLOSURE OF INVENTION

[Problem to be Solved by the Invention]

The compound of formula (II) has a good effect as an insulin sensitizing agent, a prophylactic or therapeutic agent against diabetes, a prophylactic or therapeutic agent against syndrome X, a prophylactic or therapeutic agent against diabetic complications, a prophylactic or therapeutic agent against hyperlipemia, a hypolipidemic agent, a prophylactic or therapeutic agent against obesity, a prophylactic or therapeutic agent against metabolic syndromes, an osteoporosis-treating agent, an anti-inflammatory agent, or a prophylactic or therapeutic agent against digestive system diseases, but has problems, in the production process thereof, including that: (1) a reaction solvent remains in the purification thereof; (2) the specification thereof is difficult to make uniform in the form of a drug substance for formulation; and (3) the workability of the drug substance is not favorable because of properties of the substance itself, because the compound is an oily substance having an extremely high viscosity.

Thus, there is need for a compound of formula (II) which is, in the form of a drug substance, purified so as to minimize the remaining solvent and has a uniform specification and a favorable workability, and for a process for production thereof.

[Means for Solving the Problem]

As a result of intensive studies, the present inventors have discovered that the above-described problems are solved by using a compound of formula (I) which is the calcium salt of a compound of formula (II), a hydrate thereof, a crystal of the compound of formula (I), and a crystal of the hydrate of the compound of formula (I), and also found processes for producing the same, and a compound of formula (V), a compound of formula (VI), and processes for production thereof, thereby accomplishing the invention.

The present invention relates to:
1) calcium bis[(2S)-3-[3-[(2S)-3-(4-chloro-2-cyanophenoxy)-2-fluoropropoxy]phenyl]-2-isopropoxypropionate] represented by formula (I):

[Formula 5]

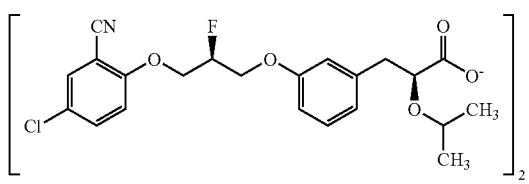

(I)

2) the compound described in 1) that is in the form of a hydrate;
3) the compound described in 1) that is in the form of a crystal;
4) the compound described in 2) or 3), represented by formula (I-a):

[Formula 6]

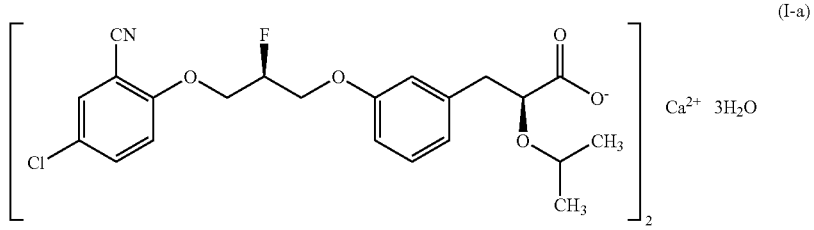

(I-a)

5) the crystal described in 4), whose powder X-ray powder diffraction pattern has peaks e.g. at diffraction angles (2θ±0.2°) of 6.6, 8.2, 21.1, and 23.0;
6) the crystal described in 4), whose infrared absorption spectrum has peaks e.g. at wave numbers (+2 cm$^{-1}$) of 1573 and 2237;
7) the crystal described in 4), whose solid state nuclear magnetic resonance spectrum (hereinafter referred to as NMR) has peaks e.g. at $^{13}$C chemical shifts (±1 ppm) of 185.1, 180.5, and 158.7;
8) a process for producing a compound represented by formula (I):

[Formula 9]

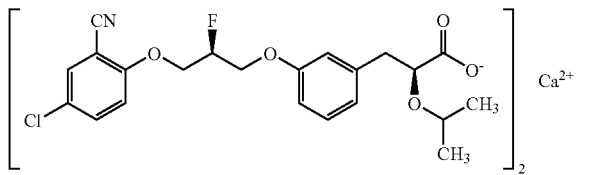

(I)

characterized by reacting a compound represented by formula (II):

[Formula 7]

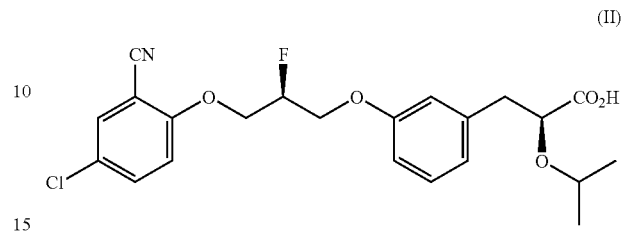

(II)

with a compound represented by formula (IV):

[Formula 8]

$CaX_2$     (IV)

(wherein $X_2$ represents a halogen atom or $OR^1$ (where $R^1$ represents a hydrogen atom or a $C_{1-3}$ alkyl group)), optionally in the presence of a base;

9) a process for producing a compound represented by formula (I):

[Formula 15]

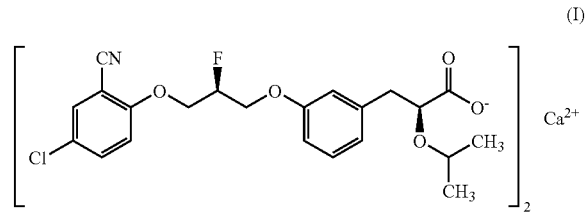

(I)

characterized by reacting a compound represented by formula (V-III):

[Formula 10]

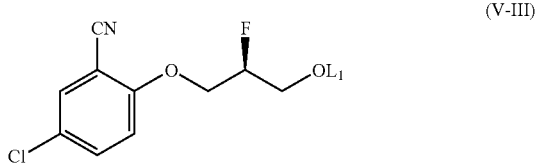

(V-III)

(wherein $L_1$ represents a hydrogen atom or a leaving group) with a compound represented by formula (VI-I):

[Formula 11]

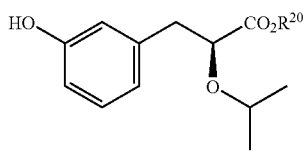

(VI-I)

(wherein $R^{20}$ represents a protecting group for a carboxyl group) in the presence of a base to make a compound represented by formula (III):

[Formula 12]

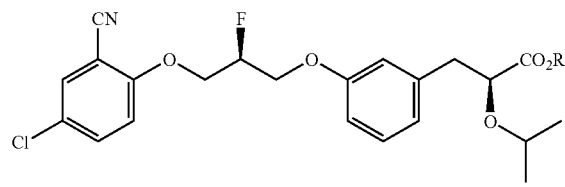

(III)

(wherein $R^{20}$ represents the same as the above), and then removing the protecting group for a carboxyl group of the compound represented by formula (III) to make a compound represented by formula (II):

[Formula 13]

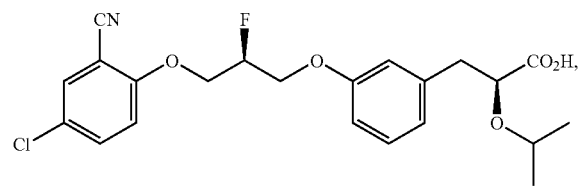

(II)

and further reacting the compound of formula (II) with a compound represented by formula (IV):

[Formula 14]

CaX$_2$   (IV)

(wherein $X_2$ represents a halogen atom or $OR^1$ (where $R^1$ represents a hydrogen atom or a $C_{1-3}$ alkyl group)), optionally in the presence of a base;

10) a compound represented by formula (V):

[Formula 16]

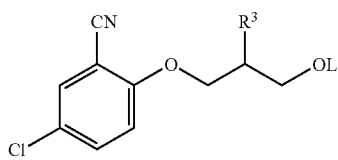

(V)

(wherein $R^3$ represents:

[Formula 17]

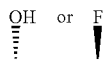

and L represents a hydrogen atom or a protecting group for a hydroxyl group or a leaving group);

11) a process for producing a compound represented by formula (V):

[Formula 21]

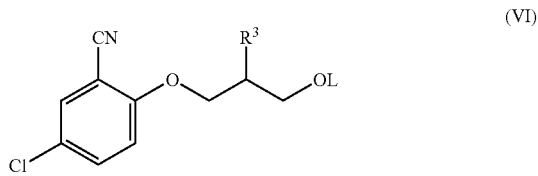

(VI)

(wherein $R^3$ represents:

[Formula 22]

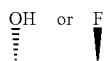

L represents a hydrogen atom or a protecting group for a hydroxyl group or a leaving group), characterized by reacting 5-chloro-2-hydroxybenzonitrile with a compound represented by formula (VII):

[Formula 18]

(VII)

(wherein $L_2$ represents a hydrogen atom or a protecting group for a hydroxyl group) to make a compound represented by formula (V-I):

[Formula 19]

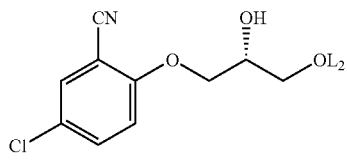

(V-I)

(wherein $L_2$ represents the same as the above), then optionally reacting the compound of formula (V-I) with a fluorinating reagent to make a compound represented by formula (V-II):

[Formula 20]

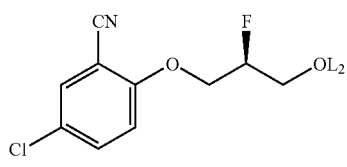

(V-II)

(wherein $L_2$ represents the same as the above), further optionally removing the protecting group for a hydroxyl group of the compound represented by formula (V-I) or the compound of formula (V-II), and further optionally converting the hydroxyl group of the compound represented by formula (V-II) into a leaving group.

12) a process for producing a compound represented by formula (V-III):

[Formula 25]

(V-III)

(wherein $L_1$ represents a hydrogen atom or a leaving group), characterized by reacting a compound represented by formula (V-I):

[Formula 23]

(V-I)

(wherein $L_2$ represents a hydrogen atom or a protecting group for a hydroxyl group) with a fluorinating reagent to make a compound represented by formula (V-II):

[Formula 24]

(V-II)

(wherein $L_2$ represents the same as the above) and then converting the protecting group for a hydroxyl group of the compound of formula (V-II) into a leaving group.

13) a compound represented by formula (VI):

[Formula 26]

(VI)

(wherein $R^2$ represents a hydrogen atom or a protecting group for a carboxyl group and $R^4$ represents a hydrogen atom or a protecting group for a hydroxyl group) or a salt thereof;

14) a process for producing a compound represented by formula (VI):

[Formula 29]

(VI)

(wherein $R^2$ and $R^4$ represent the same as the above) or a salt thereof characterized by reacting a compound represented by formula (VIII):

[Formula 27]

(VIII)

(wherein $R_2$ represents a hydrogen atom or a protecting group for a carboxyl group and $R^4$ represents a hydrogen atom or a protecting group for a hydroxyl group) with a compound represented by formula (IX):

[Formula 28]

(IX)

and optionally removing the protecting group(s);

15) a pharmaceutical composition characterized by comprising the compound described in 1); and 16) the pharmaceutical composition described in 15), which is an insulin sensitizing agent, a prophylactic or therapeutic agent against diabetes, syndrome X, diabetic complications, or hyperlipemia, a hypolipidemic agent, a prophylactic or therapeutic agent against obesity or metabolic syndromes, an osteoporosis-treating agent, an anti-inflammatory agent, or a prophylactic or therapeutic agent against digestive system diseases.

Various terms, symbols, and the like as herein described are explained below.

"Calcium bis[(2S)-3-[3-[(2S)-3-(4-chloro-2-cyanophenoxy)-2-fluoropropoxy]phenyl]-2-isopropoxypropionate] represented by formula (I):

[Formula 30]

(I)

refers to a compound in which a calcium ion and anions from the carboxyl group of the compound of formula (II) are bound each other, and may be crystalline or amorphous.

"Hydrate of the compound of formula (I)" refers to a compound in which an anhydrous molecule of the compound of formula (I) hydrated with a water molecule(s). The number of hydrating water molecules is not particularly restricted, but a trihydrate in which one anhydrous molecule of the compound hydrated with 3 molecules of water, that is, formula (I-a):

[Formula 31]

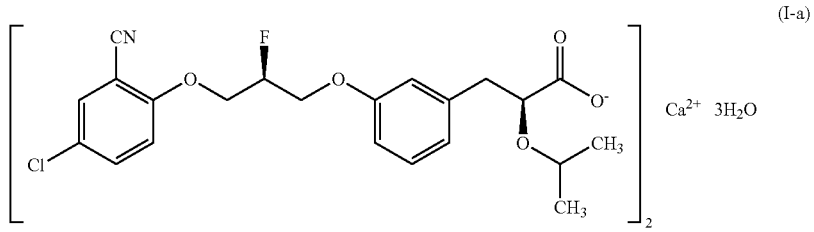

is preferable. The hydrate of the compound of formula (I) may be crystalline or amorphous, but the crystalline form thereof is preferably in terms of the stability and purification of the compound from the view point of production of a medicine. Among examples of the compound of formula (I), a preferred compound is a trihydrate crystal which represents the compound of formula (I-a), having the following physicochemical properties:

(1) the presence of peaks e.g. at diffraction angles (2θ±0.2°) of 6.6, 8.2, 21.1, and 23.0, in the powder X-ray diffraction pattern thereof;
(2) the presence of peaks e.g. at wavenumbers (±2 cm$^{-1}$) of 1573 and 2237, in the infrared absorption spectrum thereof; and
(3) the presence of peaks e.g. at $^{13}$C chemical shifts (±1 ppm) of 185.1, 180.5, and 158.7, in the solid state NMR thereof.

Definitions of terms, symbols, and the like used herein are then explained.

The term "halogen atom" refers to a fluorine atom, a chlorine atom, a bromine atom, or an iodine atom; a chlorine atom, a bromine atom, or an iodine atom, particularly a chlorine atom, is preferable, among others.

The term "$C_{1-3}$ alkyl group" refers to an alkyl group having a carbon number of 1 to 3, and examples thereof include a methyl group, an ethyl group, an n-propyl group, and an isopropyl group. A methyl group or ethyl group, particularly an ethyl group, is preferable, among others.

Examples of a base include common organic bases and inorganic bases. The term "organic base" refers to an aromatic base such as, for example, imidazole, 4-(N,N-dimethylamino)pyridine, pyridine, 2,6-lutidine, or collidine; a tertiary amine such as, for example, N-methylpiperidine, N-methylpyrrolidine, triethylamine, trimethylamine, diisopropylethylamine, cyclohexyldimethylamine, N-methylmorpholine, or 1,8-bis(dimethylamino)naphthalene; a secondary amine such as, for example, diisobutylamine, dicyclohexylamine, diethanolamine or meglumine; a basic amino acid such as, for example, arginine or histidine; an alkyllithium such as, for example, methyllithium or butyllithium; or a metal alkoxide such as, for example, sodium methoxide, sodium ethoxide, calcium methoxide, or calcium ethoxide. The term "inorganic base" refers to an alkali metal hydride such as, for example, sodium hydride or potassium hydride; an alkali earth metal hydride such as, for example, calcium hydride; an alkali metal hydroxide such as, for example, sodium hydroxide or potassium hydroxide; an alkali earth metal hydroxide such as, for example, calcium hydroxide; an alkali metal carbonate such as, for example, sodium carbonate, potassium carbonate, or cesium carbonate; or an alkali metal bicarbonate such as, for example, sodium bicarbonate.

Examples of an acid include common organic acids and inorganic acids. The term "organic acid" refers to a monocarboxylic acid such as, for example, acetic acid, propionic acid, or benzoic acid; a dicarboxylic acid such as, for example, oxalic acid; or an organic sulfonic acid such as, for example, methansulfonic acid, tosylic acid, or trifluoromethansulfonic acid. The term "inorganic acid" refers to, for example, phosphoric acid, hydrochloric acid, sulfuric acid, or nitric acid.

Examples of a leaving group include a trifluoroacetyl group, a methansulfonyl group, a trifluoromethansulfonyl group, a p-toluensulfonyl group, 3-nitrobenzensulfonyl group, and a diphenoxyphosphoryl group; a methansulfonyl group is preferable, among others.

Examples of a protecting group for a carboxyl group include a lower alkyl group such as, for example, a methyl group, ethyl group, propyl group, isopropyl group, or tert-butyl group; a halo-substituted lower alkyl group such as, for example, a 2,2,2-trichloroethyl group or 2,2,2-trifluoroethyl group; a lower alkanoyloxyalkyl group such as, for example, an acetoxymethyl group, propionyloxymethyl group, pivaloyloxymethyl group, 1-acetoxyethyl group, or 1-propionyloxyethyl group; a lower alkoxycarbonyloxyalkyl group such as, for example, a 1-(methoxycarbonyloxy)ethyl group, 1-(ethoxycarbonyloxy)ethyl group, or 1-(isopropoxycarbonyloxy)ethyl group; a lower alkenyl group such as, for example, a 2-propenyl group, 2-chloro-2-propenyl group, 3-methoxycarbonyl-2-propenyl group, 2-methyl-2-propenyl group, 2-butenyl group, or cinnamyl group; an aralkyl group such as, for example, a benzyl group, p-methoxybenzyl group, 3,4-dimethoxybenzyl group, o-nitrobenzyl group, p-nitrobenzyl group, benzhydryl group, or bis(p-methoxyphenyl)methyl group; a (5-substituted-2-oxo-1,3-dioxol-4-yl)methyl group such as, for example, a (5-methyl-2-oxo-1,3-dioxol-4-yl)methyl group; a lower alkylsilyl group such as, for example, a trimethylsilyl group or tert-butyldimethylsilyl group; and an indanyl group, a phthalidyl group, a methoxymethyl group, and the like. A methyl group and an ethyl group are particularly preferable.

Examples of a protecting for a hydroxyl group include a lower alkylsilyl group such as, for example, a trimethylsilyl group or tert-butyldimethylsilyl group; a lower alkoxymethyl group such as, for example, a methoxymethyl group or 2-methoxyethoxymethyl group; a tetrahydropyranyl group; an aralkyl group such as, for example, a benzyl group, p-methoxybenzyl group, 2,4-dimethoxybenzyl group, o-nitrobenzyl group, p-nitrobenzyl group, or trityl group; an acyl group such as, for example, a formyl group, acetyl group, or pivaloyl group; a lower alkoxycarbonyl group such as, for example, a tert-butoxycarbonyl group, 2-iodoethoxycarbonyl group, or 2,2,2-trichloroethoxycarbonyl group; an alkenyloxycarbonyl group such as, for example, a 2-propenyloxycarbonyl group, 2-chloro-2-propenyloxycarbonyl group, 3-methoxycarbonyl-2-propenyloxycarbonyl group, 2-methyl-2-propenyloxycarbonyl group, 2-butenyloxycarbonyl group, or cinnamyloxycarbonyl group; and an aralkyloxycarbonyl group such as, for example, a benzyloxycarbonyl group, p-methoxybenzyloxycarbonyl group, o-nitrobenzyloxycarbonyl group, or p-nitrobenzyloxycarbonyl group. A trityl group, a pivaloyl group, and a benzyl group are particularly preferable.

Examples of a fluorinating reagent include, for example, PBSF (perfluorobutanesulfonyl fluoride), perfluorooctanesulfonyl fluoride, DAST (diethylaminosulfur trifluoride), an alkali metal fluoride such as potassium fluoride, and sulfur tetrafluoride. PBSF is preferable, among others.

The process for producing the compound of formula (I) according to the invention is then described in detail.

The compound of formula (I) may be produced by the following production process A or B.

Production Process A

The compound of formula (I) may be produced by reacting a compound represented by formula (II):

[Formula 32]

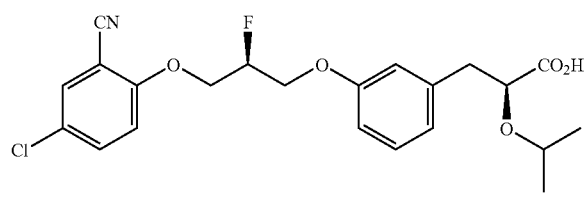

(II)

with a compound represented by formula (IV):

[Formula 33]

$CaX_2$ (IV)

(wherein $X_2$ represents a halogen atom or $OR^1$ (where $R^1$ represents a hydrogen atom or a $C_{1-3}$ alkyl group)), optionally in the presence of a base.

A solvent used in the reaction of the compound of formula (II) with the compound of formula (IV) is not particularly restricted, but is preferably an inert solvent not easily reacting with the source materials, including alcohols such as, for example, methanol, ethanol, isopropanol, and tert-butanol; ethers such as, for example, tetrahydrofuran, diethyl ether, diisopropyl ether, dioxane, and dimethoxyethane; halogenated hydrocarbons such as, for example, dichloromethane, chloroform, carbon tetrachloride, and 1,2-dichloroethane; hydrocarbons such as, for example, hexane, benzene, and toluene; ketones such as, for example, acetone and methyl ethyl ketone; nitriles such as, for example, acetonitrile; amides such as, for example, N,N-dimethylformamide, N,N-dimethylacetoamide, N-methyl-2-pyrrolidone, and hexamethylphosphorylamide; sulfoxides such as, for example, dimethylsulfoxide; water; and a mixed solvent thereof. An alcohol, a ketone, or water is preferable; for example, methanol, ethanol, acetone, water, or a mixed solvent thereof is particularly preferable, among others.

Examples of the base optionally used include the common organic bases and inorganic bases as described above; for example, a metal alkoxide and an alkali metal hydroxide are preferable. Specific examples thereof include an alkali metal hydride such as sodium hydride or potassium hydride and an alkali metal hydroxide such as lithium hydroxide, sodium hydroxide, or potassium hydroxide. However, when the compound of formula (IV) is, for example, calcium hydroxide or a calcium $C_{1-3}$ alkoxide, the reaction proceeds without further addition of a base because the compound of formula (IV) act as a base.

As used in the reaction, the compound of formula (IV) and the base may be employed in equivalent or excessive amounts relative to that of the compound of formula (II), but, in view of the smooth progress of reaction, purification treatment, and the like, are preferably used in amounts of 0.4 to 1.0 equivalent and 0.5 to 2.0 equivalents, respectively, and particularly in amounts of 0.45 to 0.55 equivalent and 0.9 to 1.1 equivalents, respectively.

The reaction time is 1 to 48 hours, preferably 3 to 18 hours. The reaction temperature is 0 to 90° C., preferably 5 to 40° C.

Production Process B

The compound of formula (I) may be produced by reacting a compound represented by formula (V-III):

[Formula 33]

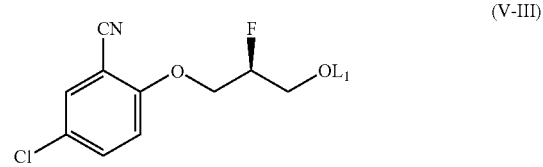

(V-III)

(wherein $L_1$ represents a hydrogen atom or a leaving group) with a compound represented by formula (VI-I):

[Formula 34]

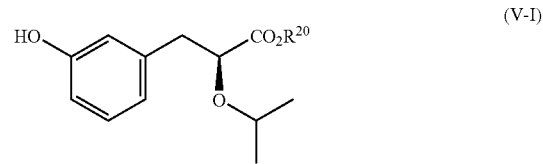

(V-I)

(wherein $R^{20}$ represents a protecting group for a carboxyl group) in the presence of a base to make a compound represented by formula (III):

[Formula 35]

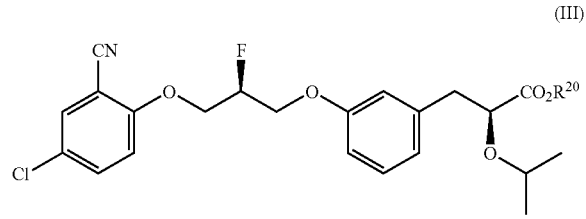

(III)

(wherein $R^{20}$ represents the same as the above), and then removing the protecting group for a carboxyl group of the compound represented by formula (III) to make a compound represented by formula (II):

[Formula 36]

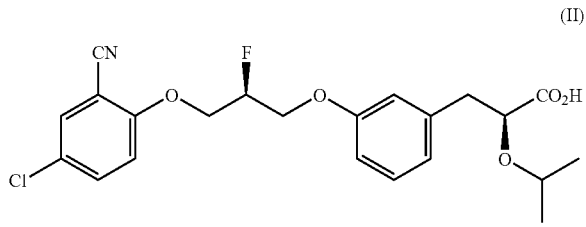

(II)

and further reacting the compound represented by formula (II) with a compound represented by formula (IV):

[Formula 37]

$$CaX_2 \quad (IV)$$

(wherein $X_2$ represents a halogen atom or —$OR^1$ (where $R^1$ represents a hydrogen atom or a $C_{1-3}$ alkyl group)), optionally in the presence of a base.

The first step of the production process is the step of reacting the compound of formula (V-III) with the compound of formula (VI-I) to produce the compound of formula (III). A solvent used in the step is not particularly restricted, but is preferably an inert solvent not easily reacting with the source materials, including, for example, alcohols such as methanol, ethanol, isopropanol, and tert-butanol; ethers such as tetrahydrofuran, diethyl ether, diisopropyl ether, dioxane, and dimethoxyethane; halogenated hydrocarbons such as dichloromethane, chloroform, carbon tetrachloride, and 1,2-dichloroethane; hydrocarbons such as hexane, benzene, and toluene; ketones such as acetone and methyl ethyl ketone; nitrites such as acetonitrile; amides such as N,N-dimethylformamide, N,N-dimethylacetoamide, N-methyl-2-pyrrolidone, and hexamethylphosphorylamide; sulfoxides such as dimethylsulfoxide; water; and a mixed solvent thereof. An amide such as N,N-dimethylformamide, N,N-dimethylacetoamide, N-methyl-2-pyrrolidone, or hexamethylphosphorylamide or a sulfoxide such as dimethylsulfoxide is preferable, among others.

Examples of the base used in the step include the common organic bases and inorganic bases as described above. Specific examples thereof include a carbonate such as sodium carbonate, potassium carbonate, or cesium carbonate; an alkoxide such as sodium methoxide or potassium tert-butoxide; and a metal phosphate such as potassium phosphate. A carbonate such as potassium carbonate is preferable, among others.

As used in the step, the compound of formula (VI-I) and the base may be used in equivalent or excessive amounts relative to that of the compound of formula (V-III), but, in view of the smooth progress of reaction, purification treatment, and the like, are preferably used in amounts of 1.0 to 3.0 equivalents and 1.0 to 3.0 equivalents, respectively, and particularly in amounts of 1.0 to 1.5 equivalents and 1.0 to 1.5 equivalents, respectively.

The reaction time is 10 to 48 hours, preferably 15 to 30 hours. The reaction temperature is 50 to 150° C., preferably 70 to 100° C.

The second step of the production process is the step of removing the protecting group for a carboxyl group of the compound of formula (III) to produce the compound of formula (II). A method for removing the protecting group for a carboxyl group varies depending on the type thereof and the stability of the compound, but may be performed by using, for example, solvolysis with an acid or a base, chemical reduction e.g. with a hydrogenated metal complex, or catalytic reduction e.g. with a palladium-carbon catalyst or a Raney-nickel catalyst, according to a method as described in a document (see Protective Groups in Organic Synthesis, T. W. Greene, John Wiley & Sons Ltd. (1981)) or a method based thereon. The base is preferably an alkali metal hydroxide such as, for example, sodium hydroxide or potassium hydroxide. A solvent used in the step is not particularly restricted, but is preferably an inert solvent not easily reacting with the source materials, including, for example, water; alcohols such as methanol, ethanol, isopropanol, and tert-butanol; ethers such as tetrahydrofuran, diethyl ether, diisopropyl ether, dioxane, and dimethoxyethane; halogenated hydrocarbons such as dichloromethane, chloroform, carbon tetrachloride, and 1,2-dichloroethane; hydrocarbons such as hexane, benzene, and toluene; ketones such as acetone and methyl ethyl ketone; nitrites such as acetonitrile; amides such as N,N-dimethylformamide, N,N-dimethylacetoamide, N-methyl-2-pyrrolidone, and hexamethylphosphorylamide; sulfoxides such as dimethylsulfoxide; or a mixture thereof. An ether such as tetrahydrofuran or dimethoxyethane is preferable, among others. The reaction temperature is 0 to 100° C., preferably 10 to 30° C. The reaction may be conducted for 1.0 to 20 hours, preferably for 3 to 10 hours.

The third step of the production process is the step of reacting the compound of formula (II) with the compound of formula (IV) to produce the compound of formula (I). This step may be carried out in the same way as that of production process A.

A compound of formula (V) useful as an intermediate raw material for the compound of formula (I) is then described.

The compound represented by formula (V):

[Formula 38]

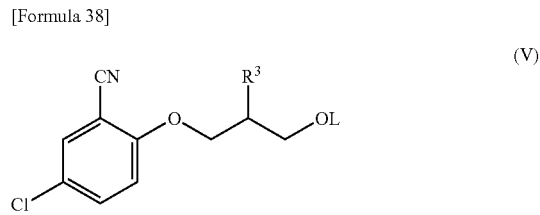

(wherein $R^3$ represents:

[Formula 39]

and L represents a hydrogen atom, a protecting group for a hydroxyl group or a leaving group) is a novel compound not yet described in the literature and encompasses a compound represented by formula (V-I):

[Formula 40]

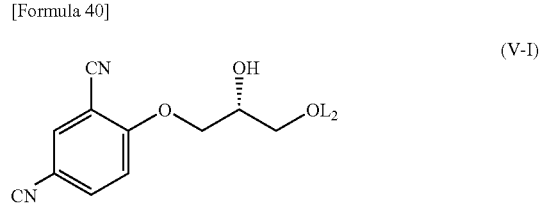

(wherein $L_2$ represents a hydrogen atom or a protecting group for a hydroxyl group), a compound represented by formula (V-II):

[Formula 41]

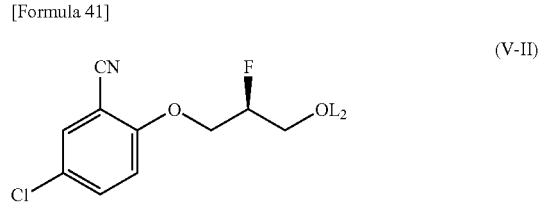

(wherein $L_2$ represents the same as the above.), or a compound of formula (V-III):

[Formula 42]

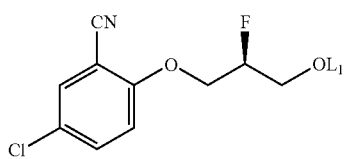

(V-III)

(wherein L₁ represents a hydrogen atom or a leaving group).

In L, L₁, and L₂, the protecting group for a hydroxyl group or the leaving group may be properly selected, and specifically, examples thereof include the protecting group for a hydroxyl group or leaving groups described above. Among others, preferred protecting groups for a hydroxyl group are, for example, aralkyl groups such as a trityl group and a benzyl group, a tetrahydropyranyl group, a trimethylsilyl group, and a tert-butylmethylsilyl group, and preferred leaving groups are, for example, a methanesulfonyl group, a toluenesulfonyl group, and a trifluoromethanesulfonyl group. It is particularly preferable that the protecting group for a hydroxyl group is, for example, a trityl group or benzyl group and the leaving group is, for example, a methanesulfonyl group.

Specific examples of the compound of formula (V), formula (V-1), formula (V-II), or formula (V-III) include 5-chloro-2-[[(2R)-2-fluoro-3-(trityloxy)propyl]oxy]benzonitrile, 5-chloro-2-[[(2S)-2-fluoro-3-(benzyloxy)propyl]oxy]benzonitrile, 5-chloro-2-[[(2R)-2-fluoro-3-(tetrahydro-2H-pyran-2-yloxy)propyl]oxy]benzonitrile, 5-chloro-2-[[(2R)-2-fluoro-3-(tert-butyldimethylsiloxy)propyl]oxy]benzonitrile, 5-chloro-2-[[(2S)-2-hydroxy-3-(trityloxy)propyl]oxy]benzonitrile, 5-chloro-2-[[(2R)-2-hydroxy-3-(benzyloxy)propyl]oxy]benzonitrile, 5-chloro-2-[[(2S)-2-hydroxy-3-(tetrahydro-2H-pyran-2-yloxy)propyl]oxy]benzonitrile, 5-chloro-2-[[(2S)-2-hydroxy-3-(tert-butyldimethylsiloxy)propyl]oxy]benzonitrile, (2R)-3-(4-chloro-2-cyanophenoxy)-2-fluoropropylmethanesulfonate, (2R)-3-(4-chloro-2-cyanophenoxy)-2-fluoropropyltoluenesulfonate, and (2S)-3-(4-chloro-2-cyanophenoxy)-2-hydroxypropyltrifluoromethanesulfonate. Among others, preferred are, for example, 5-chloro-2-[[(2R)-2-fluoro-3-(trityloxy)propyl]oxy]benzonitrile, 5-chloro-2-[[(2S)-2-hydroxy-3-(trityloxy)propyl]oxy]benzonitrile, and (2R)-3-(4-chloro-2-cyanophenoxy)-2-fluoropropylmethanesulfonate.

Then, the process for producing the compound of formula (V) according to the invention is described in detail.

The compound of formula (V) may be produced through the following production process C, and the compound of formula (V-III) through the following production process D.

Production Process C

The compound of formula (V) may be produced by reacting 5-chloro-2-hydroxybenzonitrile with a compound of formula (VII):

[Formula 43]

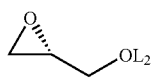

(VII)

(wherein L₂ represents a hydrogen atom or a protecting group for a hydroxyl group) to make a compound represented by formula (V-I):

[Formula 44]

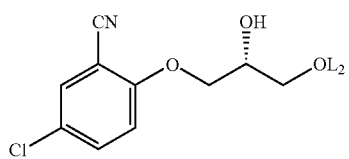

(V-I)

(wherein L₂ represents the same as the above), then optionally reacting the compound of formula (V-I) with a fluorinating reagent to make a compound represented by formula (V-II):

[Formula 45]

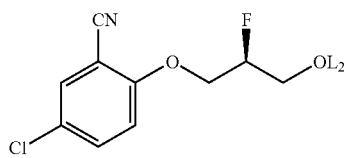

(V-II)

(wherein L₂ represents the same as the above), and further optionally removing the protecting group for a hydroxyl group of the compound of formula (V-I) or the compound of formula (V-II).

The first step of the production process is the step of reacting 5-chloro-2-hydroxybenzonitrile with a compound of formula (VII) in the presence of a base to produce the compound of formula (V-I). A solvent used in the step is not particularly restricted, but is preferably an inert solvent not easily reacting with the source materials, including, for example, alcohols such as methanol, ethanol, isopropanol, and tert-butanol; ethers such as tetrahydrofuran, diethyl ether, diisopropyl ether, dioxane, dimethoxyethane, diethoxyethane, and diglyme; halogenated hydrocarbons such as dichloromethane, chloroform, carbon tetrachloride, and 1,2-dichloroethane; hydrocarbons such as hexane, benzene, and toluene; ketones such as acetone or methyl ethyl ketone; nitriles such as acetonitrile; amides such as N,N-dimethylformamide, N,N-dimethylacetoamide, N-methyl-2-pyrrolidone, and hexamethylphosphorylamide; and sulfoxides such as dimethylsulfoxide. Among others, an ether is preferable; for example, diglyme, diethoxyethane, dimethoxyethane, or a mixed solvent thereof is particularly preferable.

Examples of the base used in the step include the common organic bases and inorganic bases as described above. Specific examples thereof include an alkali metal alkoxide such as sodium methoxide, potassium tert-butoxide, or sodium tert-butoxide, and an alkali metal hydroxide such as sodium hydroxide or potassium hydroxide. An alkali metal alkoxide such as potassium tert-butoxide is preferable, among others.

As used in the step, 5-chloro-2-hydroxybenzonitrile may be used in an equivalent or excessive amount relative to that of the compound of formula (VII), but, in view of the smooth progress of reaction, purification treatment, and the like, is preferably used in an amount of 1.0 to 3.0 equivalents and particularly in an amount of 1.0 to 1.5 equivalents. On the other hand, the base may be used in a catalytic or excessive amount relative to that of the compound of formula (VII), but, in view of the smooth progress of reaction, purification treatment, and the like, is preferably used in an amount of 0.01 to 2.0 equivalents, and particularly in an amount of 0.1 to 0.5 equivalent.

The reaction time is 10 to 64 hours, preferably 15 to 30 hours. The reaction temperature is 40 to 200° C., preferably 90 to 140° C.

Although 5-chloro-2-hydroxybenzonitrile and the compound of formula (VII) are well-known compounds, they can be also obtained using a method as described in Mariel E. Zwaagstra et al., Journal of Medicinal Chemistry, 40: 1075-1089, 1997.

The second step of the production process is the step of reacting the compound of formula (V-I) with a fluorinating reagent to make the compound of formula (V-II). A solvent used in the step is not particularly restricted, but is preferably an inert solvent not easily reacting with the source materials, including, for example, ethers such as tetrahydrofuran, diethyl ether, diisopropyl ether, dioxane, and dimethoxyethane; halogenated hydrocarbons such as dichloromethane, chloroform, carbon tetrachloride, and 1,2-dichloroethane; hydrocarbons such as hexane, benzene, and toluene; acetates such as ethyl acetate, methyl acetate, and isopropyl acetate; ketones such as acetone and methyl ethyl ketone; nitrites such as acetonitrile; amides such as N,N-dimethylformamide, N,N-dimethylacetoamide, N-methyl-2-pyrrolidone, and hexamethylphosphorylamide; sulfoxides such as dimethylsulfoxide; and a mixed solvent thereof. Among others, a hydrocarbon solvent is preferable; toluene is particularly preferable, for example.

Examples of the fluorinating reagent and base used in the step include those described above; a sulfonyl fluoride such as, for example, perfluorobutanesulfonyl fluoride, or perfluorooctanesulfonyl fluoride or a cyclic amidine such as, for example, 1,5-diazabicyclo[4.3.0]non-5-ene or 1,8-diazabicyclo[5.4.0]undec-7-ene is preferable. The fluorinating reagent and the base may be used in equivalent or excessive amounts relative to that of the compound of formula (V-I), but, in view of the smooth progress of reaction, purification treatment, and the like, are preferably used in amounts of 1.0 to 4.0 equivalents and 1.0 to 4.0 equivalents, respectively, and particularly in amounts of 1.3 to 2.0 equivalents and 1.5 to 2.5 equivalents, respectively.

The reaction time is 1 to 24 hours, preferably 1 to 4 hours. The reaction temperature is −20 to 100° C., preferably 0 to 50° C.

The third step of the production process is the step of properly removing the protecting group for a hydroxyl group of the compound of formula (V-II) and optionally converting the hydroxyl group of the compound of formula (V-II) into a leaving group to produce the compound of formula (V). The removal of the protecting groups for a hydroxyl group(s) may be carried out according to a method described in the document as is the case with that for a carboxyl group described above. For example, it can be performed using solvolysis with an acid or a base, chemical reduction e.g. with a hydrogenated metal complex, or catalytic reduction e.g. with a palladium-carbon catalyst or a Raney-nickel catalyst. Particularly, it is preferably conducted using an inorganic acid such as sulfuric acid, hydrochloric acid, or phosphoric acid; an organic sulfonic acid such as methanesulfonic acid, or toluenesulfonic acid; or an organic carboxylic acid such as trifluoroacetic acid or formic acid. Among others, sulfuric acid is most preferable. The acid may be used in a catalytic to excessive amount, preferably in a catalytic amount relative to that of the compound of formula (V-II), but, in view of the smooth progress of reaction, purification treatment, and the like, is preferably used in an amount of 0.01 to 1.0 equivalent and particularly in an amount of 0.02 to 0.10 equivalent. The reaction time is 1 to 48 hours, preferably 3 to 24 hours. The reaction temperature is −20 to 100° C., preferably 10 to 30° C. In this respect, the protecting group for a hydroxyl group can be substituted by an ordinary method as described in the above document.

Production Process D

The compound of formula (V-III) may be produced by reacting the compound represented by formula (V-I):

[Formula 46]

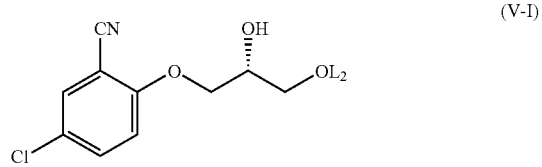

(V-I)

(wherein $L_2$ represents a hydrogen atom or a protecting group for a hydroxyl group) with a fluorinating reagent to make the compound represented by formula (V-II):

[Formula 47]

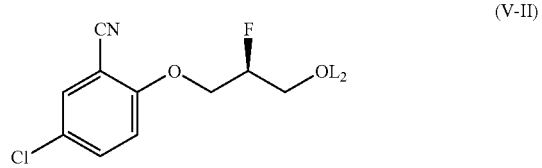

(V-II)

(wherein $L_2$ represents the same as the above) and then converting the protecting group for a hydroxyl group of the compound of formula (V-II) into a leaving group.

The first step of the production process is the step of properly reacting the compound of formula (V-I) with a fluorinating reagent to make the compound of formula (V-II), and may be carried out in the same way as the second step of production process C.

The second step of the production process is the step of properly converting the hydroxyl or protected hydroxyl group of the compound of formula (V-II) into a leaving group to produce the compound of formula (V-III).

The conversion of a hydroxyl or protected hydroxyl group into a leaving group may be carried out according to an ordinary method. Specifically, it is preferably performed by the following method. After properly removing the protecting group, the compound of formula (V-II) is reacted with an acid anhydride or an acid halide in the presence of a base. Examples of the acid anhydride or acid halide used in the step include methanesulfonic anhydride, trifluoromethanesulfonic anhydride, tosilic anhydride, methanesulfonyl chloride, trifluoromethanesulfonyl chloride, and tosilyl chloride. Examples of the base include an organic base such as triethylamine, diisopropylethylamine, or pyridine and an inorganic base such as an alkali metal carbonate (e.g. sodium carbonate), a bicarbonate (e.g. potassium bicarbonate), and a phosphate (e.g. potassium phosphate or sodium phosphate). A tertiary amine such as triethylamine is preferably used.

A solvent used in the step is not particularly restricted, but is preferably an inert solvent not easily reacting with the source materials, including, for example, ethers such as tetrahydrofuran, diethyl ether, diisopropyl ether, dioxane, and dimethoxyethane; halogenated hydrocarbons such as dichloromethane, chloroform, carbon tetrachloride, and 1,2-dichloroethane; hydrocarbons such as hexane, benzene, and toluene; acetates such as ethyl acetate, methyl acetate, and isopropyl acetate; ketones such as acetone and methyl ethyl ketone; nitrites such as acetonitrile; amides such as N,N-dimethylformamide, N,N-dimethylacetoamide, N-methyl-2- pyrrolidone, and hexamethylphosphorylamide; a sulfoxide such as dimethylsulfoxide; and a mixed solvent thereof. Among others, an ether solvent is preferable; dimethoxyethane is particularly preferable, for example.

As employed in the step, the acid anhydride or acid halide and the base may be used in equivalent or excessive amounts relative to that of the compound of formula (VII), but, in view of the smooth progress of reaction, purification treatment, and the like, are preferably used in amounts of 1.0 to 3.0 equivalents and 1.0 to 3.0 equivalents, respectively, and particularly in amounts of 1.0 to 1.5 equivalents and 1.0 to 1.6 equivalents, respectively.

The reaction time is 30 minutes to 24 hours, preferably 1 to 3 hours. The reaction temperature is −20 to 70° C., preferably −10 to 20° C.

A compound of formula (VI) useful as an intermediate raw material for the compound of formula (I) is then described.

The compound represented by formula (VI):

[Formula 48]

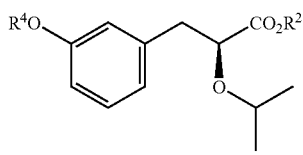

(VI)

(wherein $R^2$ represents a hydrogen atom or a protecting group for a carboxyl group, and $R^4$ represents a hydrogen atom or a protecting group for a hydroxyl group) or a salt thereof is a novel compound not yet described in the literature. In the formula (VI), the protecting group for a carboxyl group of $R^2$ and the protecting group for a hydroxyl group of $R^4$ may be properly selected, and examples thereof can include the protecting groups for a carboxyl group and for a hydroxyl group described above. Among others, preferred protecting groups for a carboxyl group are, for example, a methyl group, an ethyl group, an isopropyl group, a tert-butyl group, a benzyl group and a trimethylbenzyl group, and preferred protecting groups for a hydroxyl group are, for example, an acetoxy group, a propionyl group, a pivaloyl group, a benzoyl group, a trityl group, a benzyl group, and an ethoxycarbonyl group. It is particularly preferable that the protecting group for a carboxyl group is, for example, methyl or ethyl and the protecting group for a hydroxyl group is, for example, an acetoxy group or pivaloyl group.

Specific examples of the compound of formula (VI) include methyl (2S)-3-(3-pivaloyloxyphenyl)-2-isopropoxypropionate, methyl (2S)-3-(3-acetoxyphenyl)-2-isopropoxypropionate, and ethyl (2S)-3-(3-pivaloyloxyphenyl)-2-isopropoxypropionate; for example, methyl (2S)-3-(3-pivaloyloxyphenyl)-2-isopropoxypropionate is particularly preferable.

Among salts of the compound of formula (VI) are salts thereof in the hydroxyl group and salts thereof in the carboxyl group, which can specifically include, for example, salts thereof with alkali metals such as sodium and potassium; salts thereof with alkali earth metals such as calcium and magnesium; and salts thereof with organic bases such as tert-butylamine and cyclohexylamine. Among others, salts thereof with tert-butylamine are preferable.

Then, the process for producing the compound of formula (VI) is described in detail.

The compound of formula (VI) may be produced through production process E.

Production Process E

The compound of formula (VI) may be produced by reacting a compound of formula (VIII):

[Formula 49]

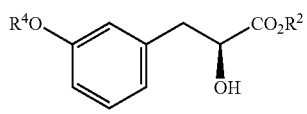

(VIII)

(wherein $R^2$ represents a hydrogen atom or a protecting group for a carboxyl group and $R^4$ represents a hydrogen atom or a protecting group for a hydroxyl group) with a compound represented by formula (IX):

[Formula 50]

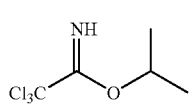

(IX)

in the presence of an acid and optionally converting the hydrogen atom of the hydroxyl and/or carboxyl group, the protecting group of a carboxyl group, and/or the protecting group of a hydroxyl group of the resultant compound into a desired substituent selected from the group consisting of a hydrogen atom, a protecting group for a carboxyl group, and a protecting group for a hydroxyl group, by a method of protecting or deprotecting a carboxyl group and/or a method of protecting or deprotecting a hydroxyl group which are conventionally used.

A solvent used in the reaction of the compound of formula (VIII) with the compound of formula (IX) is not particularly restricted, but is preferably an inert solvent not easily reacting with the source materials, including, for example, ethers such as tetrahydrofuran, diethyl ether, diisopropyl ether, dioxane, and dimethoxyethane; halogenated hydrocarbons such as dichloromethane, chloroform, carbon tetrachloride, and 1,2-dichloroethane; hydrocarbons such as hexane, heptane, benzene, and toluene; ketones such as acetone and methyl ethyl ketone; nitrites such as acetonitrile; amides such as N,N-dimethylformamide, N,N-dimethylacetoamide, N-methyl-2-pyrrolidone, and hexamethylphosphorylamide; sulfoxides such as dimethylsulfoxide; and a mixed solvent thereof. Among others, an ether or a hydrocarbon is preferable; 1,2-dimethoxyethane, heptane, hexane, or a mixed solvent thereof is particularly preferable, for example.

Examples of the acid used in the step include those described above; an inorganic acid such as sulfuric acid or phosphoric acid, an organic sulfonic acid such as trifluoromethanesulfonic acid, methanesulfonic acid, or benzenesulfonic acid, or a carboxylic acid such as trifluoroacetic acid or formic acid. Among others, an organic sulfonic acid such as trifluoromethanesulfonic acid is preferable.

As used in the reaction, the compound of formula (IX) and the acid may be used in equivalent or excessive amounts or in catalytic amounts relative to that of the compound of formula (VII), but, in view of the smooth progress of reaction, purification treatment, and the like, are preferably used in amounts of 1.5 to 4.0 equivalents and 0.1 to 1.0 equivalent, respectively, and particularly in amounts of 2.5 to 3.5 equivalents and 0.3 to 0.7 equivalent, respectively.

The reaction time is 6 to 48 hours, preferably 15 to 24 hours. The reaction temperature is −20 to 70° C., preferably 0 to 25° C.

The compound of formula (VIII) may be produced according to a process described in Kenneth N. F. et al., Journal of Organic Chemistry, 21:1149, 1956, and the compound of formula (IX) may be produced from commercial trichloroacetonitrile and isopropanol by applying a method described in Alan Armstrong et al., Tetrahedron Letters, 29: 2483, 1988.

In order to demonstrate the usefulness of the compound of formula (I), a crystalline trihydrate of the compound of formula (I) was then selected as a typical compound from compounds of formula (I-a) to perform a test for determining the following properties and the amount of impurities by HPLC, using the compound of formula (II) as control. <<Description>>

(1) Test method

Visual observation was carried out according to the general rules in the Japanese Pharmacopoeia Fourteenth Edition. The results are shown in Table 1.

(2) Results

TABLE 1

| Compound to be tested | Description |
| --- | --- |
| Compound of formula (I-a) | White powder |
| Compound of formula (II) | Colorless clear liquid with high viscosity |

<<HPLC impurities (except stereoisomers)>>

(1) Measurement method

About 1.5 mg each of the compound of formula (I-a) and the compound of formula (II) were weighed. Acetonitrile/water/70% perchloric acid (v/v/v =468:532:1) was added for dissolution and a concentration was adjusted to about 1.5 mg/mL. The content (%) of impurities was calculated from obtained peak area under the following HPLC conditions.

(2) Measurement Conditions

Measurement was carried out using the column and mobile phase shown in Table 2 below. Specifically, mobile phase A and mobile phase B were fed at a rate of 46:54 (v/v) for 20 minutes, followed by feeding them while changing the rate of mobile phase A to mobile phase B so as to reach 0:100 (v/v) in the subsequent 20 minutes.

TABLE 2

| Column | L-column ODS (4.6 mm I.D. × 150 mm) |
| --- | --- |
| Mobile phase | Acetonitrile/water/70% perchloric acid (Mobile phase A: v/v/v = 100:900:1) (Mobile phase B: v/v/v = 900:100:1) |
| Detection | UV279 nm |
| Flow rate | 1.0 mL/min |
| Injection volume | 10 μL |
| Column temperature | 45° C. |

(3) Results

TABLE 3

| Compound to be tested | Amount (%) of impurities |
| --- | --- |
| Compound of formula (I-a) | 0.34 |
| Compound of formula (II) | 2.44 |

These results show that the compound of formula (I) typified by the compound of formula (I-a) 10 occurs as a white solid and a compound with favorable properties, containing impurities to a lesser extent relative to the compound of formula (II).

As a typical example of the compound of formula (I), the compound of formula (I-a) produced in Example 1 was subjected to the measurement of X-ray powder diffraction, infrared absorption spectrum, and solid state nuclear magnetic resonance spectrum. The results are shown below.

(X-ray Powder Diffraction)

(1) Measurement method

The sample was pulverized using an agate mortar, and subjected to measurement under the following conditions employing an X-ray powder diffractometer.

(2) Measurement conditions

Target, tube current, and tube voltage: Cu, 200 mA, and 40 kV

Filter: monochromator

Scanning rate: 2°/min

Measurement range: 5 to 40° (2θ)

Divergent slit: 0.5°

Receiving slit: 0.3 mm

Scattering slit: 0.5°

(3) A pattern of X-ray Powder Diffraction is shown in FIG. 1.

(4) Typical diffraction angles (2θ±0.2°): e.g. 6.6, 8.2, 21.1, and 23.0

(Infrared Spectrophotometry)

(1) Measurement Method and Conditions

The measurement was carried out according to the potassium bromide disk method under the infrared absorption spectrometry of the General Test Procedures in the Japanese Pharmacopoeia Fourteenth Edition.

(2) An Infrared Absorption Spectrum is Shown in FIG. 2.

(3) Typical Wavenumbers (±2 $cm^{-1}$): e.g. 1,573 and 2,237

(Solid State NMR Spectroscopy)

(1) Measurement Method

Using a solid state NMR spectrometer, $^{13}C$ solid state NMR measurement was carried out under the following conditions.

(2) Measurement Conditions

Temperature: room temperature (approximately 22°C.)

Reference material: hexamethylbenzene (external reference: 17.35 ppm)

Measurement nucleus: $^{13}C$ (75.497791 MHz)

Pulse delay time: 4 sec

Pulse mode: TOSS measurement (3) An NMR Spectrum is Shown in FIG. 3.

(4) Typical Chemical Shifts (±1 ppm): e.g. 185.1, 180.5, and 158.7

The compound of formula (I) according to the invention improves insulin resistance through an agonist effect on PPAR, but the use thereof is not limited to an insulin sensitizing agent because it has agonist effects on PPARs α, β, and γ (which, for example, may be based on dual-agonist effects on PPARs α and γ, or on triple-agonist effects on PPARs α, β, and γ). Thus, the compound is useful as an insulin sensitizing agent, a prophylactic or therapeutic agent against diabetes, a prophylactic or therapeutic agent against syndrome X, a prophylactic or therapeutic agent against diabetic complications, a prophylactic or therapeutic agent against hyperlipemia, a hypolipidemic agent, a prophylactic or therapeutic agent against obesity, a prophylactic or therapeutic agent against metabolic syndromes, an osteoporosis-treating agent, an anti-inflammatory agent, or a prophylactic or therapeutic agent against digestive system diseases.

The dosage form of the compound of the invention when used as any of the above-described agents may be selected from various forms including, for example, oral preparations such as tablets, capsules, powders, granules, and solutions, and sterile liquid parenteral preparations such as solutions and suspensions.

Solid preparations may be produced, directly therefrom, in the form of tablets, capsules, granules, or powders, or may be also prepared using appropriate additives. Such additives include, for example, saccharides such as lactose and glucose, starches such as corn, wheat, and rice, fatty acids such as stearic acid, inorganic salts such as sodium metasilicate, magnesium aluminate, and anhydrous calcium phosphate, synthetic polymers such as polyvinylpyrrolidone and polyalkylene glycol, fatty acid salts such as calcium stearate and magnesium stearate, alcohols such as stearyl alcohol and benzyl alcohol, synthetic cellulose derivatives such as methylcellulose, carboxymethyl cellulose, ethylcellulose, and hydroxypropyl methylcellulose, and other commonly used additives such as water, gelatin, talc, vegetable oil, and gum arabic.

These solid preparations such as tablets, capsules, granules, and powders may generally contain 0.1 to 100% by weight, preferably 0.1 to 20% by weight of an active ingredient. The liquid preparations may be produced in the form of suspensions, syrups, or injections, using appropriate additives commonly used in liquid preparations including water, alcohols, or plant-derived oils such as soybean oil, peanut oil, and sesame oil.

Appropriate solvents particularly for parenteral administration through intramuscular, intravenous, or subcutaneous injection include, for example, distilled water for injection, lidocaine hydrochloride aqueous solution (for intramuscular injection), physiological saline, glucose aqueous solution, ethanol, liquid for intravenous injection (e.g. an aqueous solution such as citric acid or sodium citrate), electrolyte solution (e.g. for intravenous drip or intravenous injection), or a mixture thereof.

These injectables may also take the form of the powder as it is or with appropriate additives added dissolved before use, in addition to that preliminarily dissolved. These injection solutions may generally contain 0.001 to 10% by weight, preferably 0.005 to 5% by weight of active ingredient.

Fluids such as suspensions or syrups for oral administration may contain 0.005 to 5% by weight of active ingredient.

The practically preferred dose of the compound of the invention may be changed depending on the type of the compound to be used, the kinds of blended compositions, administration frequency, the specific site to be treated, and the disease state of a patient. For example, the daily dose per adult is 100 µg to 10 g. In this respect, the administration frequency varies depending on the method of administration and symptoms, but it may be administered in a single dose or in 2 to several divided doses daily.

[Advantages of the Invention]

According to the invention, the compound of formula (I) of the present invention has agonist effects on PPARs α, β, and γ (which, for example, may be based on dual-agonist effects on PPARs α and γ, or on triple-agonist effects on PPARs α, β, and γ), and is therefore useful as an insulin sensitizing agent, a prophylactic or therapeutic agent against diabetes, a prophylactic or therapeutic agent against syndrome X, a prophylactic or therapeutic agent against diabetic complications, a prophylactic or therapeutic agent against hyperlipemia, a hypolipidemic agent, a prophylactic or therapeutic agent against obesity, a prophylactic or therapeutic agent against metabolic syndromes, an osteoporosis-treating agent, an anti-inflammatory agent, or a prophylactic or therapeutic agent against digestive system diseases.

BEST MODE FOR CARRYING OUT THE INVENTION

Examples

The present invention is further concretely described below with reference to Examples. However, it will be appreciated that the invention is not intended to be limited only to these Examples.

For the purpose of the NMR measurement, the meanings of abbreviations are as follows.

s: singlet
d: doublet
dd: double doublet
ddd: double double doublet
t: triplet
dt: double triplet
dtt: double triple triplet
q: quartet
m: multiplet
br: broad
J: coupling constant
Hz: hertz
$CDCl_3$: deuterated chloroform
$CD_3OD$: deuterated methanol
$D_2O$: deuterium oxide
$DMSO\text{-}d_6$: deuterated dimethylsulfoxide For the purpose of reaction formulae and the like, the meanings of abbreviations are as follows.

t-Bu: tert-butyl group
Et: ethyl group
Me: methyl group
Ms: methanesulfonyl group
Piv: pivaloyl group
Tf: trifluoromethanesulfonyl group
Tr: Trityl group
KTB: potassium tert-butoxide
PBSF: perfluorobutanesulfonyl fluoride
DBU: 1,8-diazabicyclo[5.4.0]undec-7-ene Example 1

Calcium bis[(2S)-3-[3-[(2S)-3-(4-chloro-2-cyanophenoxy)-2-fluoropropoxy]phenyl]-2-isopropoxypropionate] trihydrate Example 1-(1)

(2S)-3-(3-hydroxyphenyl)-2-hydroxypropionic acid (S)-phenethylamine salt

[Formula 51]

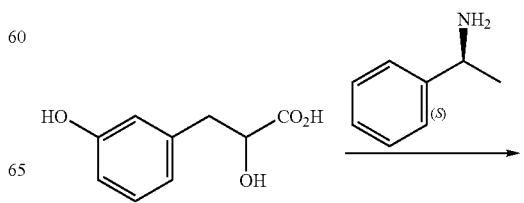

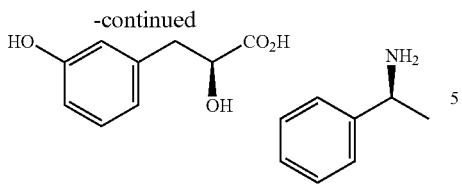

An ethanol (125 mL) solution of (S)-phenethylamine (16.6 g, 0.137 mol) was added to an ethanol (250 mL) solution of 3-(3-hydroxyphenyl)-2-hydroxypropionic acid (25 g, 0.137 mol) at room temperature, followed by stirring the reaction mixture at the same temperature for 17 hours. The precipitated crystals were filtered and washed with ethanol, followed by air drying at 40° C. for 30 hours to obtain 17.9 g of the title compound (yield: 43%, optical purity: 95% ee).

$^1$H-NMR(CD$_3$OD)δ:1.59 (3H, d, J=6.8 Hz), 2.68 (1H, dd, J=13.9, 8.6 Hz), 3.03 (1H, dd, J=13.9, 3.4 Hz), 4.08 (1H, dd, J=8.3, 3.4 Hz), 4.40 (1H, q, J=6.8 Hz), 6.57 (1H, ddd, J=7.1, 1.5, 1.5 Hz), 6.73 (1H, s), 6.74 (1H, d, J=7.8 Hz), 7.05 (1H, dd, J=7.8, 7.1 Hz), 7.35~7.45 (5H, m) cl Example 1-(2)

Methyl (2S)-3-(3-hydroxyphenyl)-2-hydroxypropionate

[Formula 52]

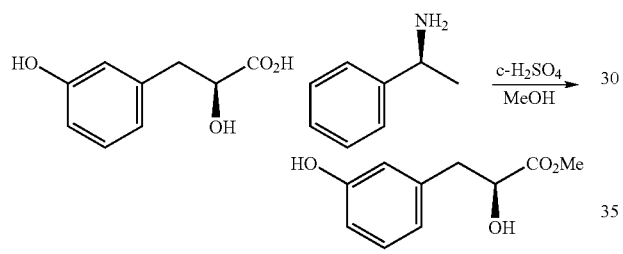

To a solution of sulfuric acid (3.88 L, 72 mol) and methanol (32 L), (2S)-3-(3-hydroxyphenyl)-2-hydroxypropionic acid (S)-phenethylamine salt (17 kg, 56 mol) was charged under cooling. After heating the reaction mixture at 60° C. for 1 hour, tert-butylmethyl ether (163 L) and sodium chloride solution (55 L) were added to the reaction mixture, followed by stirring and then separating the mixture. To the aqueous layer was added tert-butylmethyl ether (51 L) for separating. The organic layers were then combined. The resultant organic layer was washed with a 1N hydrochloric acid aqueous solution (28 L) and then with a 7% sodium bicarbonate aqueous solution (28 L). The separated organic layer was subjected to vacuum concentration to obtain 8.93 kg of the title compound in the form of yellow oily matter (yield: 81%).

$^1$H-NMR(CD$_3$OD)δ:2.82 (1H, dd, J=13.7, 7.8 Hz), 2.96 (1H, dd, J=13.7, 4.9 Hz), 3.68 (3H, s), 4.33 (1H, dd, J=7.8, 4.9 Hz), 6.11 (1H, dd, J=8.1, 2.4 Hz), 6.67 (1H, s), 6.67 (1H, d, J=8.1 Hz), 7.07 (1H, dd, J=8.1, 8.1 Hz).

Example 1-(3)

Methyl (2S)-3-(3-pivaloyloxyphenyl)-2-hydroxypropionate

[Formula 53]

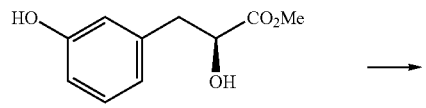

Methyl (2S)-3-(3-hydroxyphenyl)-2-hydroxypropionate (8.93 kg, 45.1 mol) was dissolved in tert-butylmethyl ether (133 L), and triethylamine (12.7 L, 91 mol) was added to the reaction mixture at room temperature, followed by cooling. Pivaloyl chloride (5.89 L, 48 mol) was added dropwise to the reaction mixture at an internal temperature of 2° C. After the end of the dropwise addition, the reaction mixture was stirred at 10° C. for 17 hours. To the reaction mixture was added 43 L of a 1N hydrochloric acid aqueous solution before stirring, followed by allowing to stand and then separating the mixture. The organic layer was washed twice each with a 0.25N sodium hydroxide aqueous solution (45 L) and water (45 L), and further washed with 42 L of a 5% sodium chloride solution, and then the organic layer was subjected to vacuum concentration at 50° C. After that, 1,2-dimethoxyethane (45 L) was added to the residue and then again subjected to vacuum concentration to obtain 11.0 kg of the title compound (yield: 86%).

$^1$H-NMR(CDCl$_3$)δ:1.35 (9H, s), 2.81~2.86 (1H, m), 2.96 (1H, dd, J=14.5, 8.2 Hz), 3.13 (1H, dd, J=14.5, 4.2 Hz), 3.78 (3H, s), 4.43~4.48 (1H, m), 6.92~6.96 (2H, m), 7.07 (1H, d, J=7.6 Hz), 7.30 (1H, dd, J=7.6, 7.6 Hz).

Example 1-(4)

Methyl (2S)-3-(3-pivaloyloxyphenyl)-2-isopropoxypropionate

[Formula 54]

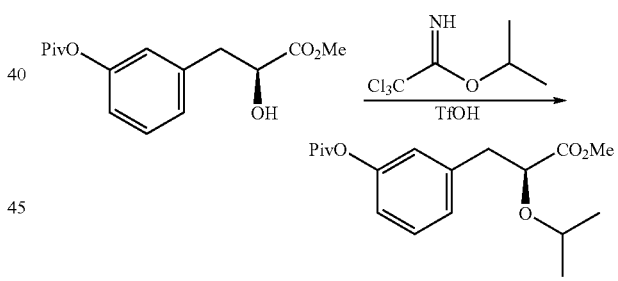

Methyl (2S)-3-(3-pivaloyloxyphenyl)-2-hydroxypropionate (11 kg), 2,2,2-trichloro-1-isopropoxyethanimine (20 kg, 98 mol), 1,2-dimethoxyethane (10 L), and heptane (44 L) were mixed and stirred, and the resultant solution was cooled to 7° C. Trifluoromethanesulfonic acid (2.36 kg, 15.7 mol) was added dropwise to the reaction mixture over a period of 36 minutes, followed by stirring the reaction mixture at 25° C. for 19 hours. The reaction mixture was cooled to 7° C., to which heptane (66 L) was then added. The reaction mixture was then stirred for 45 minutes, followed by filtering off a white crystal of trichloroacetoamide. Water (55 L) was added to the filtrate for separating. Then, the organic layer was washed with a 5% sodium bicarbonate aqueous solution (52 L) twice and with water (55 L), followed by vacuum concentration to obtain 12.1 kg of the title compound (yield: 96%).

$^1$H-NMR(CDCl$_3$)δ:0.95 (3H, d, J=6.5 Hz), 1.14 (3H, d, J=6.5 Hz), 1.35 (9H; s), 2.93 (1H, dd, J=14.5, 8.2 Hz), 3.01 (1H, dd, J=14.5, 4.2 Hz), 3.44~3.54 (1H, m), 3.72 (3H, s), 4.06 (1H, dd, J=8.2, 4.2 Hz), 6.92 (1H, d, J=7.6 Hz), 6.95 (1H, s), 7.10 (1H, d, J=7.6 Hz), 7.28 (1H, dd, J=7.6, 7.6 Hz).

Example 1-(5)

Methyl (2S)-3-(3-hydroxyphenyl)-2-isopropoxypropionate

[Formula 55]

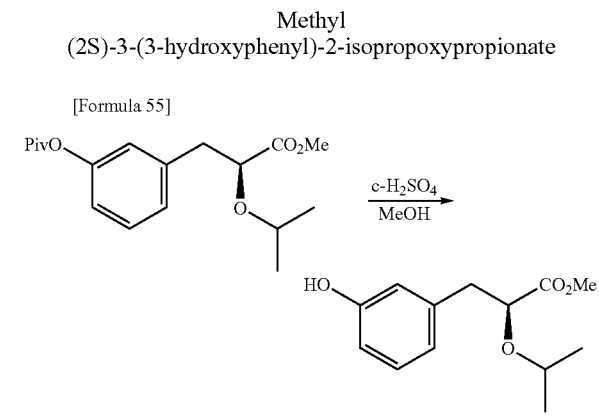

Methyl (2S)-3-(3-pivaloyloxyphenyl)-2-isopropoxypropionate (12.1 kg, 37.5 mol) was dissolved in methanol (49 L) and then cooled, followed by adding dropwise concentrated sulfuric acid (3 L) to the reaction mixture at an internal temperature of 8.8° C. After stirring the reaction mixture at 60° C. for 19 hours, toluene (121 L) and water (61 L) were added to the mixture for separating. The aqueous layer was again extracted with toluene (121 L). The organic layers were then combined. The resultant organic layer was washed with a 5% sodium bicarbonate aqueous solution (57 L) and with water (61 L) and then dried with anhydrous magnesium sulfate, followed by vacuum concentration to obtain 8.81 kg of the title compound in the form of oily matter (yield: 99%).

$^1$H-NMR (CDCl$_3$)γ: 0.97 (3H, d, J=6.5 Hz), 1.14 (3H, d, J=6.5 Hz), 2.89 (1H, dd, J=14.5, 8.2 Hz), 2.97 (1H, dd, J=14.5, 4.2 Hz), 3.46~3.56 (1H, m), 3.73 (3H, s), 4.10 (1H, dd, J=8.2, 4.2 Hz), 5.75 (1H, brs), 6.72 (1H, d, J=7.6 Hz), 6.77 (1H, s), 6.80 (1H, d, J=7.6 Hz), 7.14 (1H, dd, J=7.6, 7.6 Hz).

Example 1-(6)

(2S)-3-(3-Hydroxyphenyl)-2-isopropoxypropionic acid

[Formula 56]

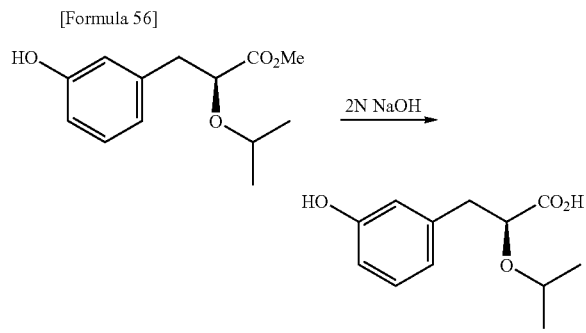

Methyl (2S)-3-(3-hydroxyphenyl)-2-isopropoxypropionic (8.5 kg, 36 mol) was dissolved in methanol (24 L) and a 2N sodium hydroxide aqueous solution (41 L) was added dropwise to the reaction mixture over a period of 10 minutes, followed by stirring the mixture at 26° C. for 3.5 hours. Tert-butylmethyl ether (85 L) was added to the reaction mixture to separate an aqueous layer. Tert-butylmethyl ether (85 L) was added to the resultant aqueous layer and concentrated sulfuric acid (9 L) was added for acidification, followed by separating the solution. The organic layer was subjected to vacuum concentration to obtain 7.61 kg of the title compound in the form of oily matter (yield: 95%).

$^1$H-NMR (CDCl$_3$)δ: 1.03 (3H, d, J=6.5 Hz), 1.17 (3H, d, J=6.5 Hz), 2.90 (1H, dd, J=14.5, 8.2 Hz), 3.06 (1H, dd, J=14.5, 4.2 Hz), 3.52~3.62 (1H, m), 4.14 (1H, dd, J=8.2, 4.2 Hz), 6.73 (1H, d, J=7.6 Hz), 6.75 (1H, s), 6.80 (1H, d, J=7.6 Hz), 7.15 (1H, dd, J=7.6, 7.6 Hz).

Example 1-(7)

(2S)-3-(3-Hydroxyphenyl)-2-isopropoxypropionic acid tert-butylamine salt

[Formula 57]

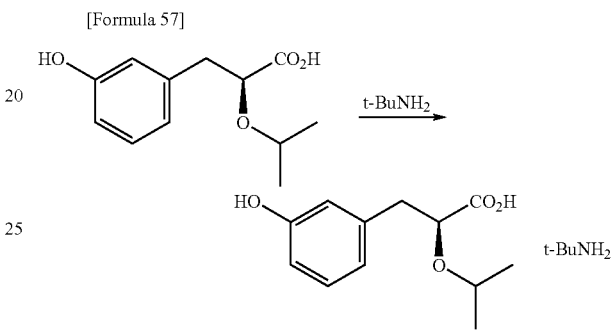

(2S)-3-(3-Hydroxyphenyl)-2-isopropoxypropionic acid (7.6 kg, 34 mol) was dissolved in 1,2-dimethoxyethane (131 L), then tert-butylamine (3.9 L, 37 mol) was added dropwise to the reaction mixture at 20° C. over a period of 15 minutes. The reaction mixture was stirred at 75° C. for 2 hours and cooled, followed by separating the generated crystal by filtration. The crystals were subjected to vacuum drying at 40° C. for 23 hours to obtain 9.04 kg of the title compound (yield: 90%).

$^1$H-NMR (D$_2$O)δ: 0.86 (3H, d, J=6.5 Hz), 0.97 (3H, d, J=6.5 Hz), 1.22 (9H, s), 2.64 (1H, dd, J=14.5, 8.2 Hz), 2.79 (1H, dd, J=14.5, 4.2 Hz), 3.36~3.46 (1H, m), 3.92 (1H, dd, J=8.2, 4.2 Hz), 6.62 (1H, d, J=7.6 Hz), 6.67 (1H, s), 6.74 (1H, d, J=7.6 Hz), 7.09 (1H, dd, J=7.6, 7.6 Hz).

Example 1-(8)

Methyl (2S)-3-(3-hydroxyphenyl)-2-isopropoxypropionate

[Formula 58]

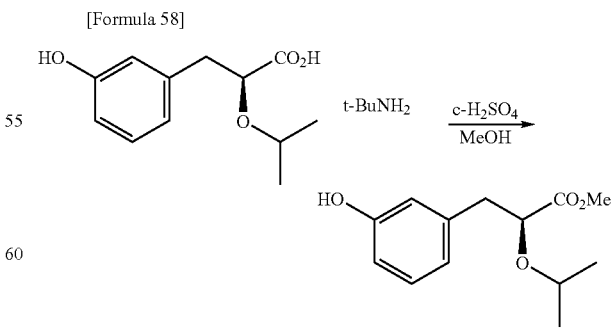

(2S)-3-(3-Hydroxyphenyl)-2-isopropoxypropionic acid tert-butylamine salt (8.2 kg, 28 mol) was dissolved in methanol (41 L), and then the reaction mixture was cooled to 10° C.

Concentrated sulfuric acid (1.9 L, 36 mol) was added to the reaction mixture at 10 to 20° C. over a period of 5 minutes. The reaction mixture was stirred at 60° C. for 3 hours, followed by adding tert-butylmethyl ether (164 L) and a 10% sodium chloride solution (41 L) to separate an organic layer. Then, the organic layer was washed sequentially with the 10% sodium chloride solution (41 L), a 7% sodium bicarbonate aqueous solution (16 L), and water (41 L), followed by vacuum concentration to obtain 6.62 kg of the title compound (yield: 100%). The $^1$H-NMR data thereof coincided with that of the compound of Example 1-(5).

Example 1-(9)

5-Chloro-2-[[(2S)-2-hydroxy-3-(trityloxy)propyl]oxy]benzonitrile

[Formula 59]

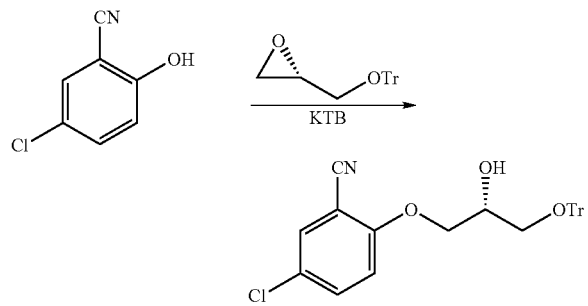

To a diglyme (1.1 L) solution of 5-chloro-2-hydroxybenzonitrile (the compound of Reference Example 1; 270 g, 1.8 mol) and (2S)-2-[(trityloxy)methyl]oxirane (465 g, 1.47 mol) was added potassium tert-butoxide (33 g, 0.29 mol) at room temperature, followed by stirring the reaction mixture at 105° C. for 23 hours. The reaction mixture was cooled with ice, to which toluene (2 L) and a 1N sodium hydroxide aqueous solution (1.35 L) were then added to separate an organic layer. The organic layer was washed 3 times each sequentially with the 1N sodium hydroxide aqueous solution (1.35 L) and warm water (3 L), followed by vacuum concentration. Toluene (3 L) was added to the concentrate, to dissolved it, followed by cooling and filtering the precipitated crystal to obtain 590 g of the title compound (yield: 85%).

$^1$H-NMR (CDCl$_3$)δ: 2.50 (1H, d, J=6.1 Hz), 3.35~3.45 (2H, m), 4.05~4.20 (3H, m), 6.91 (1H, d, J=9.0 Hz), 7.22~7.33 (8H, m), 7.38~7.53 (9H, m).

Example 1-(10)

5-Chloro-2-[[(2R)-2-fluoro-3-(trityloxy)propyl]oxy]benzonitrile

[Formula 60]

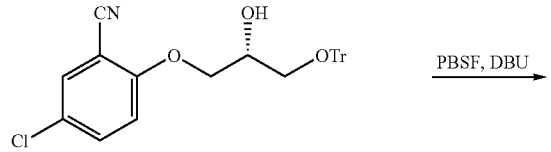

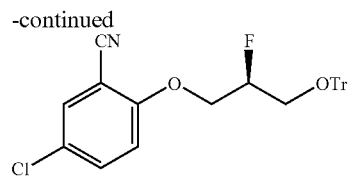

Perfluorobutanesulfonyl fluoride (594 g, 2.0 mol) and 1,8-diazabicyclo[5.4.0]undec-7-ene (282 g, 1.85 mol) were added to an ice-cooled toluene (14.5 L) solution of 5-chloro-2-[[(2S)-2-hydroxy-3-(trityloxy)propyl]oxy]benzonitrile (580 g, 1.23 mol) at the same temperature in a nitrogen atmosphere, followed by stirring the reaction mixture at 35° C. Toluene (2.0 L) and a 1N sodium hydroxide aqueous solution (1.7 L) were added to the reaction mixture to separate an organic layer which was then washed 3 times each sequentially with the 1N sodium hydroxide aqueous solution (1.7 L) and water (1.1 L), followed by vacuum concentration. Methanol (3.3 L) was added to the resultant crude crystal, followed by heating the reaction mixture to 44° C. before cooling to room temperature. The precipitated crystal was filtered and then washed with methanol (0.75 L), followed by drying at 50° C. for 18 hours to obtain 470 g of the title compound (yield: 81%).

$^1$H-NMR (CDCl$_3$)δ: 3.35~3.62 (2H, m), 4.21~4.41 (2H, m), 4.91 (1H, br d, J=47.4 Hz), 6.92 (1H, d, J=9.1 Hz), 7.20~7.55 (17H, m).

Example 1-(11)

5-Chloro-2-[((2S)-2-fluoro-3-hydroxypropyl)oxy]benzonitrile

[Formula 62]

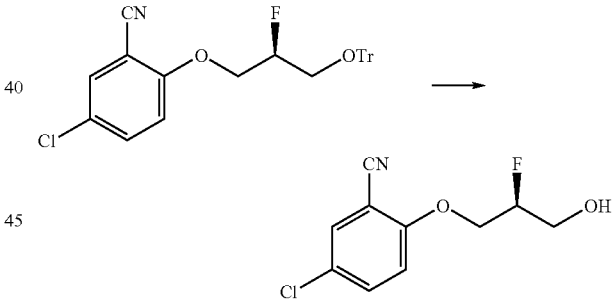

5-Chloro-2-[[(2R)-2-fluoro-3-(trityloxy)propyl]oxy]benzonitrile (460 g, 0.97 mol) was suspended in a toluene-methanol mixture (4.8 L/3.22 L) at room temperature and then concentrated sulfuric acid (3.1 mL, 0.06 mol) was added to the reaction mixture, followed by stirring the reaction mixture at the same temperature for 18.5 hours. A 1N sodium hydroxide aqueous solution was added to the reaction mixture at room temperature to adjust the pH to 14 or more, followed by subjecting the reaction mixture to vacuum concentration. Ethyl acetate (2.1 L) and water (1.2 L) were added to the residue to separate an organic layer, followed by washing the organic layer twice with water (1.2 L) before vacuum concentration. Ethyl acetate (0.7 L) was added to the resultant crude crystal, which was then heated to 60° C. for complete dissolution. Heptane (3.8 L) was then added to the reaction mixture, followed by cooling and the filtration of the precipitated crystal to obtain 196 g of the title compound (yield: 88%).

$^1$H-NMR (CDCl$_3$)δ: 1.99 (1H, t, J=6.1 Hz), 3.91~4.09 (2H, m), 4.35 (2H, dd, J=19.3, 4.6 Hz), 4.96 (1H, dtt, J=47.1, 4.6, 4.6 Hz), 6.96 (1H, d, J=8.8 Hz), 7.52 (1H, dd, J=8.8, 2.6 Hz), 7.54 (1H, d, J=2.6 Hz).

Example 1-(12)

(2R)-3-(4-Chloro-2-cyanophenoxy)-2-fluoropropyl-methanesulfonate

[Formula 63]

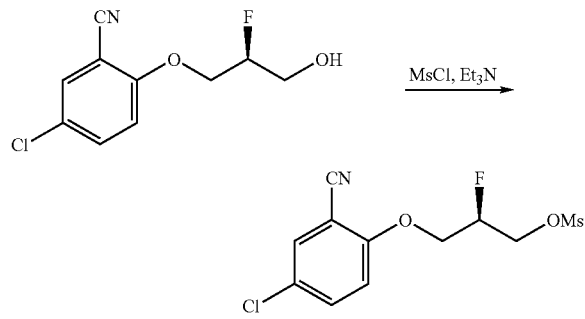

Triethylamine (87 g, 0.86 mol) was added to a dimethoxyethane (494 mL) solution of 5-chloro-2-[((2S)-2-fluoro-3-hydroxypropyl)oxy]benzonitrile (124 g, 0.538 mol) at room temperature and then cooled with ice, followed by adding methanesulfonic acid chloride (86 g, 0.75 mol) to the reaction mixture. The reaction mixture was stirred at the same temperature for 1 hour, to which tert-butylmethyl ether (1 L) and water (1.5 L) were then added to separate an organic layer. The organic layer was washed with a 5% sodium chloride solution (0.74 L) and then dried with anhydrous magnesium sulfate, followed by vacuum concentration to obtain 168 g of the title compound (yield: 95%).

$^1$H-NMR (CDCl$_3$)δ: 3.10 (3H, s), 4.30~4.43 (2H, m), 4.55~4.67 (2H, m), 5.14 (1H, dtt, J=46.1, 4.6, 4.6 Hz), 6.96 (1H, d, J=8.8 Hz), 7.53 (1H, dd, J=8.8, 2.7 Hz), 7.59 (1H, d, J=2.7 Hz).

Example 1-(13)

Methyl (2S)-3-[3-[(2S)-3-(4-chloro-2-cyanophenoxy)-2-fluotopropoxy]phenyl]-2-isopropoxypropionate

[Formula 64]

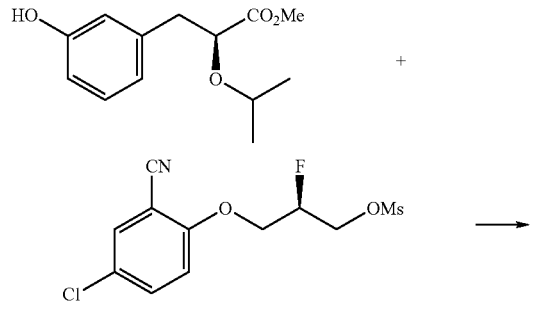

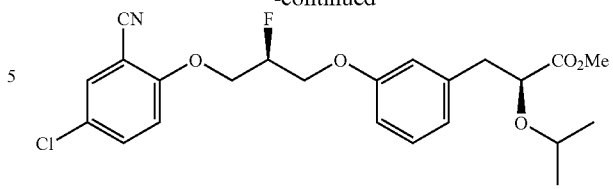

(2R)-3-(4-Chloro-2-cyanophenoxy)-2-fluoropropyl-methanesulfonate (156 g, 0.51 mol), methyl (2S)-3-(3-hydroxyphenyl)-2-isopropoxypropionate (121 g, 0.51 mol), and potassium carbonate (73.7 g, 0.53 mol) were suspended in N,N-dimethylformamide (624 mL) at room temperature, followed by stirring the reaction mixture at 80° C. for 28 hours. After cooling the reaction mixture with ice, tert-butylmethylether (1.56 L) and water (2.34 L) were added to separate an organic layer. The organic layer was washed sequentially with a 1N sodium hydroxide aqueous solution (1.56 L), a sodium chloride solution (1.56 L), a 1N hydrochloric acid aqueous solution (1.56 L), and water (1.56 L), and subjected to vacuum concentration to obtain 212 g of the title compound (orange color oil, yield: 82%).

$^1$H-NMR (CDCl$_3$)δ: 0.95 (3H, d, J=6.1 Hz), 1.14 (3H, d, J=6.1 Hz), 2.82~3.01 (2H, m), 3.45~3.55 (1H, m), 3.73 (3H, s), 4.07 (1H, dd, J=8.8, 4.9 Hz), 4.27~4.50 (4H, m), 5.20 (1H, dtt, J=46.7, 4.7, 4.7 Hz), 6.82 (1H, dd, J=8.1, 1.8 Hz), 6.84 (1H, d, J=1.8 Hz), 6.87 (1H, d, J=8.1 Hz), 6.98 (1H, d, J=8.8 Hz), 7.21 (1H, dd, J=8.1, 8.1 Hz), 7.51 (1H, dd, J=8.8, 2.1 Hz), 7.57 (1H, d, J=2.1 Hz).

Example 1-(14)

(2S)-3-[3-[(2S)-3-(4-Chloro-2-cyanophenoxy)-2-fluoropropoxy]phenyl]-2-isopropoxypropionic acid

[Formula 65]

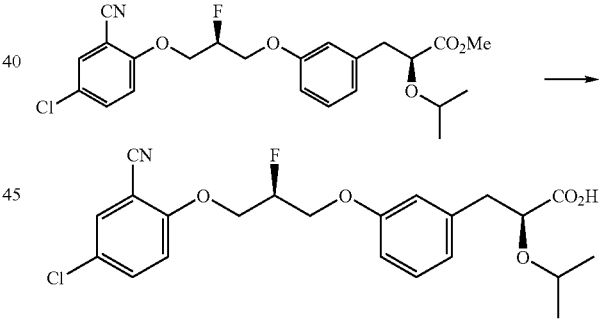

Methyl (2S)-3-[3-[(2S)-3-(4-chloro-2-cyanophenoxy)-2-fluoropropoxy]phenyl]-2-isopropoxypropionate (186 g, 0.41 mol) was suspended in tetrahydrofuran (928 mL) and water (928 mL), followed by adding dropwise a 2N NaOH aqueous solution (309 mL, 0.62 mmol) to the reaction mixture at room temperature and the mixture was stirred for 3.5 hours. Tert-butylmethyl ether (1,856 mL) and water (928 mL) were added to the reaction mixture to separate an aqueous layer. Tert-butylmetyl ether (1,856 mL) was added to the aqueous layer, followed by adding dropwise a 2N hydrochloric acid aqueous solution (371 mL, 0.74 mol) at room temperature to separate an organic layer. The organic layer was washed with water (928 mL) and then subjected to vacuum concentration to obtain 185 g of the title compound (yield: 90%).

$^1$H-NMR (CDCl$_3$)δ: 1.05 (3H, d, J=6.1 Hz), 1.15 (3H, d, J=6.1 Hz), 2.95 (1H, dd, J=14.0, 7.6 Hz), 3.11 (1H, dd, J=14.0, 4.4 Hz), 3.52~3.63 (1H, m), 4.13 (1H, dd, J=7.6, 4.4 Hz), 4.28~4.50 (4H, m), 5.20 (1H, dtt, J=46.7, 4.6, 4.6 Hz), 6.83 (1H, d, J=5.9 Hz), 6.84 (1H, s), 6.88 (1H, d, J=7.3 Hz), 6.99 (1H, d, J=8.8 Hz), 7.23 (1H, dd, J=7.3, 5.9 Hz), 7.51 (1H, dd, J=8.8, 2.4 Hz), 7.54 (1H, d, J=2.4 Hz).

Example 1-(15)

Calcium bis[(2S)-3-[3-[(2S)-3-(4-chloro-2-cyanophenoxy)-2-fluoropropoxy]phenyl]-2-isopropoxypropionate]trihydrate

[Formula 66]

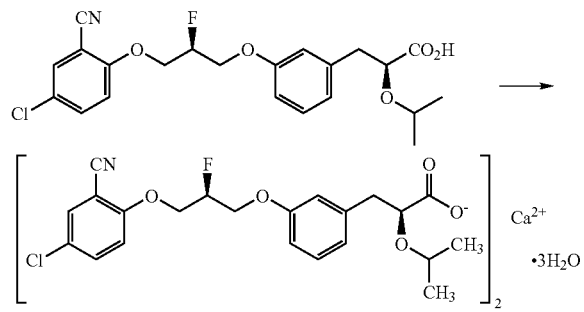

A methanol solution (500 mL) of calcium chloride dihydrate (23.8 g, 0.16 mol) was added to an acetone (1750 mL) solution of (2S)-3-[3-[(2S)-3-(4-chloro-2-cyanophenoxy)-2-fluoropropoxy]phenyl]-2-isopropoxypropionic acid (140 g, 0.32 mol) at 40° C. After confirming the dissolution, methanol (1,250 mL) was added to the reaction mixture. The reaction mixture was heated to 40° C., to which a 5N sodium hydroxide aqueous solution (64 mL, 0.32 mol) was then added dropwise over a period of 8 minutes and then water (134 ml) was added dropwise over a period of 29 minutes. The reaction mixture was cooled to 15° C., followed by filtering the precipitated crystal before vacuum drying at 40° C. to obtain 136.5 g of the title compound (yield: 93%).

$^1$H-NMR (DMSO-$d_6$)δ: 0.81 (3H, d, J=6.0 Hz), 1.02 (3H, d, J=6.0 Hz), 2.62 (1H, dd, J=9.6, 14.4 Hz), 2.95 (1H, d, J=13.2 Hz), 3.57 (1H, Quint, J=6.0 Hz), 3.77 (1H, brs), 4.27-4.61 (4H, m), 5.25 (1H, dt, J=2.8, 48.8 Hz), 6.77 (1H,dd, J=2.0, 8.0 Hz) 6.84-6.88 (2H, m), 7.16 (1H, t, J=8.0 Hz), 7.36 (1H, d, J=8.8 Hz), 7.75 (1H, dd, J=2.8, 9.2 Hz), 7.95 (1H, d, J=3.2 Hz)

Example 2

Calcium bis[(2S)-3-[3-[(2S)-3-(4-chloro-2-cyanophenoxy)-2-fluoropropoxy]phenyl]-2-isopropoxypropionate]trihydrate Example 2-(1)

(4S)-4-Benzyl-3-(2-isopropoxyacetyl)-1,3-oxazolidin-2-one

[Formula 67]

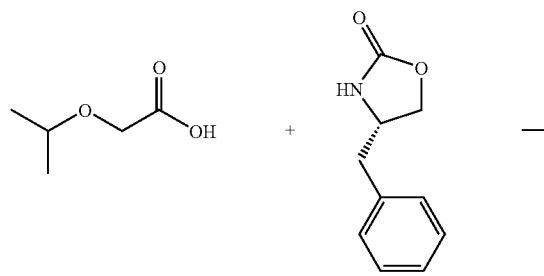

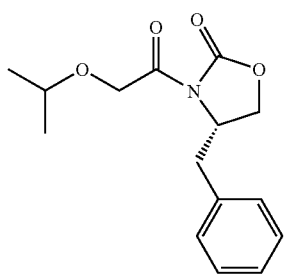

A tetrahydrofuran (6 L) solution of 140 g of 2-isopropoxyacetic acid and 540 mL of triethylamine was cooled to −20° C., to which a tetrahydrofuran (100 mL) solution of 145 g of 2,2-dimethylpropanoyl chloride was added dropwise, followed by stirring the reaction mixture at −10 to −20° C. for 3 hours. The reaction mixture was cooled to −30° C., to which 80 g of anhydrous lithium chloride and then 225 g of (4S)-4-benzyl-1,3-oxazolidin-2-one was added, followed by stirring the reaction mixture overnight at room temperature. The reaction mixture was filtered and subjected to vacuum concentration. The residue was dissolved in 3 L of ethyl acetate, washed with a saturated sodium bicarbonate aqueous solution (1.5 L), and dried with anhydrous magnesium sulfate. The solvent was distilled off under a reduced pressure, and the residue was purified using silica gel column chromatography to obtain 196 g of the title compound in the form of colorless oily matter from a hexane-ethyl acetate (5:1→2:1)-eluted fraction.

$^1$H-NMR (CDCl$_3$)δ: 1.17 (6H, d, J=6.0 Hz), 2.81 (1H, dd, J=9.5, 13.4 Hz), 3.35 (1H, dd, J=3.2,13.4 Hz), 3.74 (1H, sept, J=6.0 Hz), 4.24 (1H, dd, J=3.5,9.3 Hz), 4.29 (1H, t, J=9.3 Hz), 4.65 (1H, d, J=19.5 Hz), 4.69 (1H, m), 4.70 (1H, d, J=19.5 Hz), 7.22 (2H, d, J=7.2 Hz), 7.30-7.45 (3H, m).

Example 2-(2)

(4S)-4-Benzyl-3-[(2S,3R)-3-(3-benzyloxyphenyl)-3-hydroxy-2-isopropoxypropionyl]-1,3-oxazolidin-2-one

[Formula 68]

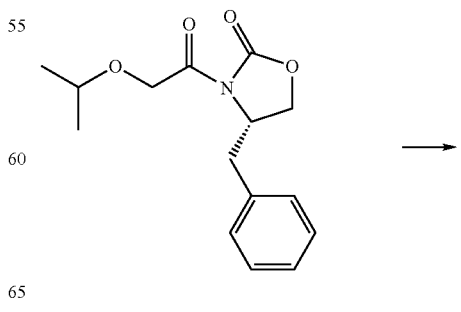

-continued

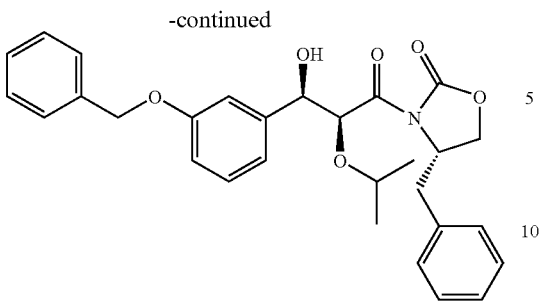

A toluene (2.4 L) solution of 150 g of (4S)-4-benzyl-3-(2-isopropoxyacetyl)oxazolidin-2-one and 90 mL of triethylamine was cooled to −70° C., to which 550 mL of dibutylboron triflate (1M dichloromethane solution) was added dropwise at an internal temperature of −70° C. or less. After the dropwise addition, the internal temperature was increased to 0° C. and the reaction mixture was stirred at 0° C. for 30 minutes, followed by again cooling to −70° C. A dichloromethane (300 mL) solution of 121 g of 3-benzyloxybenzaldehyde was added to the reaction mixture using a cannula, followed by increasing the internal temperature to 0° C. over a period of 40 minutes. The reaction mixture was stirred at 0° C. for 1.5 hours, to which 1 L of methanol, 1.5 L of pH 7 buffer (sodium dihydrogenphosphate-citric acid) and 250 mL of hydrogen peroxide (30% aqueous solution) were then added, followed by stirring the solution at room temperature for 30 minutes. Subsequently, the reaction mixture was extracted with ethyl acetate (3 L). The organic layer was washed with a saturated sodium chloride solution (1.5 L), and then dried with anhydrous magnesium sulfate, followed by distilling off the solvent under a reduced pressure. The residue was purified using silica gel column chromatography to obtain 274.3 g of the title compound in the form of colorless oily matter from a hexane-ethyl acetate (2:1→3:2)-eluted fraction.

$^1$H-NMR (CDCl$_3$)δ: 1.11 (3H, d, J=6.0 Hz), 1.19 (3H, d, J=6.0 Hz), 2.75 (1H, dd, J=9.6, 13.2 Hz), 3.08 (1H, d, J=5.6 Hz), 3.26 (1H, dd, J=3.2, 13.2 Hz), 3.60-3.69 (2H, m), 3.99 (1H, dd, J=1.6, 8.8 Hz), 4.27-4.33 (1H, m), 4.84 (1H, t, J=5.6 Hz), 5.07 (2H, s), 5.44 (1H, d, J=5.2 Hz), 6.88-6.90 (1H, m), 7.00 (1H, d, J=7.6 Hz), 7.09 (1H, t, J=2.0 Hz), 7.16-7.24 (3H, m), 7.28-7.35 (6H, m), 7.39-7.43 (2H, m).

Example 2-(3)

(4S)-4-Benzyl-3-[(2S)-3-(3-hydroxyphenyl)-2-isopropoxypropionyl]-1,3-oxazolidin-2-one

[Formula 69]

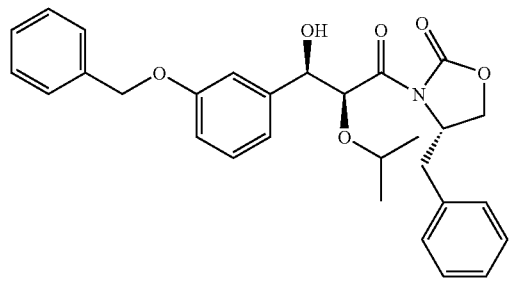

274.3 g of (4S)-4-benzyl-3-[(2S,3R)-3-(3-benzyloxyphenyl)-3-hydroxy-2-isopropoxypropionyl]-1,3-oxazolidin-2-one was dissolved in 700 mL of pyridine, and 60.7 mL of methanesulfonyl chloride was added dropwise under cooling with ice. The reaction mixture was stirred at room temperature for 2.5 hours, followed by distilling off pyridine under a reduced pressure. 3 L of ethyl acetate was added to the residue, which was then washed sequentially with 1N hydrochloric acid (1 L) and a saturated sodium chloride solution (1.5 L), followed by drying the organic layer with anhydrous magnesium sulfate. The solvent was distilled off under a reduced pressure to obtain (1R,2S)-3-((4S)-4-benzyl-2-oxo-1,3-oxazolidin-3-yl)-1-(3-benzyloxyphenyl)-2-isopropoxy-3-oxopropylmethanesulfonate. This compound was dissolved in a mixture of 3.6 L of ethanol and 400 mL of tetrahydrofuran, to which 60 g of 10% palladium-carbon was added, followed by stirring the reaction mixture overnight at room temperature in a hydrogen atmosphere. The reaction mixture was filtered, and the filtrate was concentrated. The residue was diluted in ethyl acetate (3 L), which was then washed with a saturated sodium bicarbonate aqueous solution (1.5 L), followed by drying the organic layer with anhydrous magnesium sulfate before distilling off the solvent under a reduced pressure. The resultant residue was purified using silica gel column chromatography to obtain 129.9 g of the title compound in the form of colorless oily matter from a hexane-ethyl acetate (2:1)-eluted fraction.

$^1$H-NMR (CDCl$_3$)δ: 1.04 (3H, d, J=6.0 Hz), 1.16 (3H, d, J=6.0 Hz), 2.78 (1H, dd, J=9.6, 13.2 Hz), 2.86-2.96 (2H, m), 3.31 (1H, dd, J=2.4, 13.6 Hz), 3.53 (1H, Sept, J=6.0 Hz), 4.01 (1H, t, J=8.0 Hz), 4.13 (1H, dd, J=2.4, 9.2 Hz), 4.50-4.55 (1H, m), 5.22 (1H, s), 5.39 (1H, dd, J=5.2, 8.4 Hz), 6.71 (1H, dd, J=2.4, 8.0 Hz), 6.82 (1H, t, J=2.0 Hz), 6.87 (1H, d, J=7.6 Hz), 7.14 (1H, t, J=8.0 Hz), 7.18-7.23 (2H, m), 7.27-7.35 (3H, m)

Example 2-(4)

Ethyl (2S)-3-(3-hydroxyphenyl)-2-isopropoxypropionate

[Formula 70]

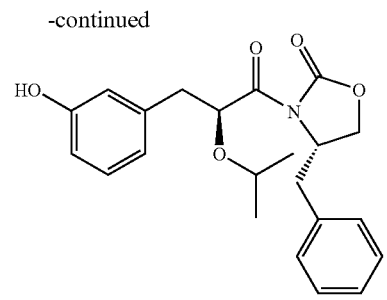

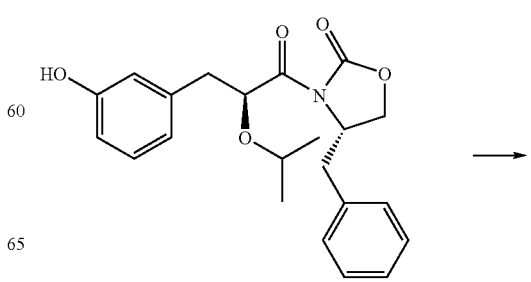

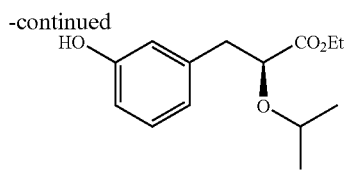

129.9 g of (4S)-4-benzyl-3-[(2S)-3-(3-hydroxyphenyl)-2-isopropoxypropionyl]-1,3-oxazolidin-2-one was dissolved in 2 L of tetrahydrofuran, to which 140 mL of 30% hydrogen peroxide solution was added. Under cooling with ice, 700 mL of 1N lithium hydroxide solution was added dropwise, followed by stirring at 0° C. for 1 hour. To the reaction mixture was added 1N hydrochloric acid (500 mL), to which a sodium sulfite aqueous solution (10%, 500 mL) was then added slowly. The mixture was poured into a separating funnel to separate a tetrahydrofuran layer, followed by making the aqueous layer at pH 2 with 1N hydrochloric acid before extraction 3 times with ethyl acetate (1 L). The organic layers were combined and washed with a saturated sodium chloride solution (1.5 L) before drying the organic layer with anhydrous magnesium sulfate, followed by distilling off the solvent under a reduced pressure to obtain 130 g of (2S)-3-(3-hydroxyphenyl)-2-isopropoxypropionic acid. This compound was dissolved in 1 L of N,N-dimethylformamide, to which 67.8 g of potassium bicarbonate and 100 mL of ethyl iodide were sequentially added under cooling with ice, followed by stirring the reaction mixture at room temperature for 3 days. The reaction mixture was diluted with ethyl acetate, and washed sequentially with 1N hydrochloric acid and a saturated sodium chloride solution. The organic layer was dried with anhydrous magnesium sulfate, followed by distilling off the solvent under a reduced pressure. The residue was purified using silica gel column chromatography to obtain 61.8 g of the title compound in the form of colorless oily matter from a hexane-ethyl acetate (3:1)-eluted fraction.

$^1$H-NMR (CDCl$_3$)δ: 0.98 (3H, d, J=6.4 Hz), 1.16 (3H, d, J=6.4 Hz), 1.24 (3H, t, J=7.2 Hz), 2.89 (1H, dd, J=8.8, 14.0 Hz), 2.97 (1H, dd, J=4.8, 13.6 Hz), 3.52 (1H, Sept, J=6.0 Hz), 4.05 (1H, dd, J=4.8, 8.8 Hz), 4.12-4.19 (2H, m), 5.01 (1H, br), 6.09-6.72 (1H, m), 6.81-6.83 (1H, m), 6.75 (1H, t, J=1.6 Hz), 7.15 (1H, t, J=7.6 Hz).

Example 2-(5)

Ethyl (2S)-2-isopropoxy-3-[3-[(2S)-2-oxiran-2-yl-methoxy]phenyl]propionate

[Formula 71]

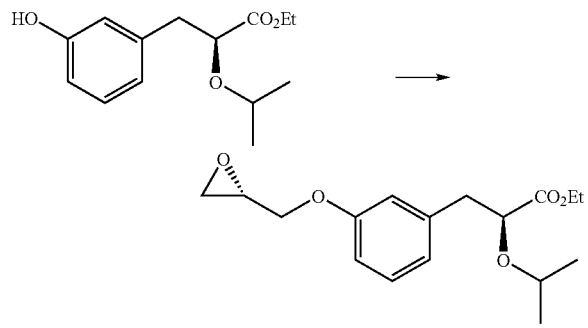

60.8 g of ethyl (2S)-3-(3-hydroxyphenyl)-2-isopropoxypropionate was dissolved in 600 mL of N,N-dimethyl- formamide, to which 46.6 g of potassium carbonate, 7.3 g of cesium fluoride, and 81.3 g of (S)-glycidyl nosylate were then added, followed by stirring the reaction mixture overnight at room temperature. To the reaction mixture was further added 1.3 g of cesium fluoride, which was then stirred overnight at room temperature. To the reaction mixture were added 500 ml each of water, saturated ammonium chloride aqueous solution, and 1N hydrochloric acid, followed by extraction with ethyl acetate (2.5 L). The organic layer was washed with a saturated sodium chloride solution (1 L) and dried with anhydrous magnesium sulfate, followed by distilling off the solvent under a reduced pressure. The residue was purified using silica gel column chromatography to obtain 69.2 g of the title compound in the form of colorless oily matter from a hexane-ethyl acetate (4:1)-eluted fraction.

$^1$H-NMR (CDCl$_3$)δ: 0.96 (3H, d, J=6.0 Hz), 1.15 (3H, d, J=6.0 Hz), 1.24 (3H, t, J=7.2 Hz), 2.76 (1H, dd, J=2.8, 4.8 Hz), 2.87-2.98(3H, m), 3.33-3.37(1H, m), 3.50(1H, Sept, J=6.0 Hz), 3.95(1H, dd, J=6.0, 11.2 Hz), 4.04(1H, dd, J=4.8, 9.2 Hz), 4.14-4.22(3H, m), 6.78(1H, dd, J=2.8, 8.4 Hz), 6.83 (1H, d, J=2.0 Hz), 6.86(1H, d, J=7.6 Hz), 7.19(1H, t, J=8.4 Hz).

Example 2-(6)

Ethyl (2S)-3-{3-[(2R)-3-(4-chloro-2-cyanophenoxy)-2-hydroxypropoxy]phenyl}-2-isopropoxypropionate

[Formula 72]

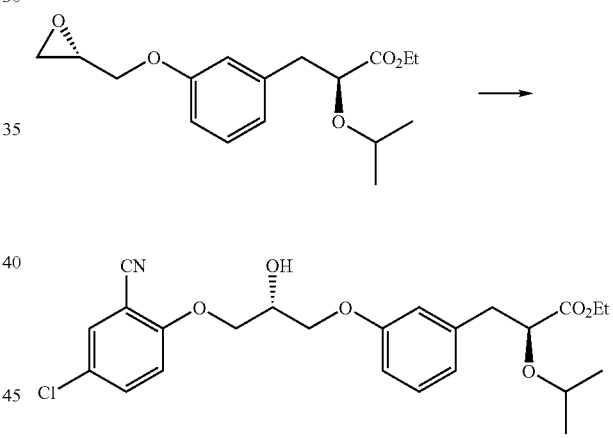

51 g of ethyl (2S)-2-isopropoxy-3-[3-[(2S)-2-oxiran-2-yl-methoxy]phenyl]propionate was dissolved in 400 mL of ethanol, to which 45.6 g of 4-chloro-2-cyanophenol and 6.85 g of potassium carbonate were then added, followed by stirring at 50° C. for 2 days. The reaction mixture was cooled to room temperature, to which water (500 mL) and 1N hydrochloric acid (500 mL) were then added, followed by extraction with ethyl acetate (2 L). The organic layer was washed with a saturated sodium chloride solution (700 mL) and dried with anhydrous magnesium sulfate, followed by distilling off the solvent under a reduced pressure. The residue was purified using silica gel column chromatography to obtain 65.3 g of the title compound in the form of colorless oily matter from a hexane-ethyl acetate (2:1)-eluted fraction.

$^1$H-NMR(CDCl$_3$)δ: 0.96(3H, d, J=6.0 Hz), 1.14(3H, d, J=6.0 Hz), 1.25(3H, t, J=6.0 Hz), 2.79(1H, d, J=6.0 Hz), 2.87-3.01(2H, m), 3.51(1H, Sept, J=6.0 Hz), 4.04(1H, dd, J=4.8, 9.2 Hz), 4.16-4.30(6H, m), 4.43(1H, Sept, J=5.2 Hz), 6.80(1H, dd, J=2.0, 8.0 Hz), 6.84(1H, s), 6.88(1H, d, J=8.0

Hz), 6.98(1H, d, J=8.0 Hz), 7.20(1H, t, J=8.0 Hz), 7.50(1H, dd, J=2.0, 8.0 Hz), 7.54(1H, d, J=2.0 Hz).

Example 2-(7)

(2S)-3-[3-[(2S)-3-(4-chloro-2-cyanophenoxy)-2-fluoropropoxy]phenyl]-2-isopropoxypropionic acid

[Formula 73]

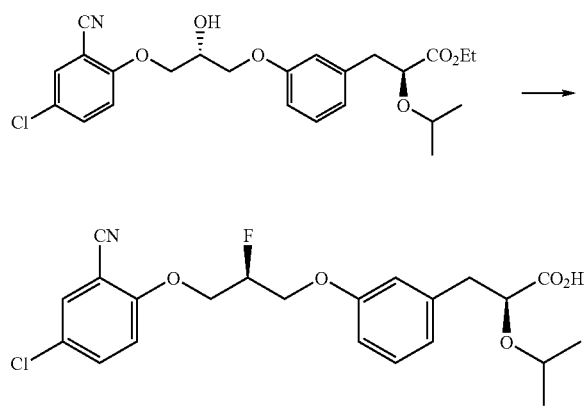

65.3 g of ethyl (2S)-3-{3-[(2R)-3-(4-chloro-2-cyanophenoxy)-2-hydroxypropoxy]phenyl}-2-isopropoxypropionate was dissolved in 1.3L of dichloromethane, which was then cooled to −68° C. Then 54 mL of diethylaminosulfur trifluoride was added, followed by stirring at room temperature for 4 days. The reaction mixture was cooled with ice, to which water (1 L) and a saturated sodium chloride solution (1 L) were then added, followed by extraction with ethyl acetate (4 L). The organic layer was washed with the saturated sodium chloride solution (2 L) and dried with anhydrous magnesium sulfate, followed by distilling off the solvent under a reduced pressure. The residue was purified using silica gel column chromatography to obtain 33 g of ethyl (2S)-3-[3-[(2S)-3-(4-chloro-2-cyanophenoxy)-2-fluoropropoxy]phenyl]-2-isopropoxypropionate from a hexane-ethyl acetate (7:1→5:1)-eluted fraction. This compound was dissolved in 400 mL of ethanol, to which 107 mL of 2N sodium hydroxide aqueous solution was then added, followed by stirring the reaction mixture at room temperature for 2 hours. The reaction mixture was cooled with ice, to which water (500 mL) and a 5N hydrochloric acid aqueous solution (50 mL) were then added before further adding water (1 L), followed by extraction with ethyl acetate (2.5 L). The organic layer was washed with the saturated sodium chloride solution (1 L) and dried with anhydrous magnesium sulfate, followed by distilling off the solvent under a reduced pressure. The residue was purified using silica gel column chromatography to obtain 27.6 g of the title compound in the form of colorless oily matter from a hexane-ethyl acetate (3:1→1:1)-eluted fraction.

$^1$H-NMR(CDCl$_3$)δ:1.04(3H, d, J=6.4 Hz), 1.17(3H, d, J=6.0 Hz), 2.94(1H, dd, J=8.0, 13.6 Hz), 3.10(1H, dd, J=3.6, 13.2 Hz), 3.57(1H, Sept, J=4.0 Hz), 4.15(1H, brs), 4.29-4.50 (4H, m), 5.20(1H, dsept, J=4.4, 46.4 Hz), 6.81-6.85(2H, m), 6.88(1H, d, J=7.6 Hz), 6.98(1H, d, J=8.8 Hz), 7.22(1H, dt, J=8.0, 9.2 Hz), 7.50-7.54(2H, m)

Example 2-(8)

Calcium bis[(2S)-3-[3-[(2S)-3-(4-chloro-2-cyanophenoxy)-2-fluoropropoxy]phenyl]-2-isopropoxypropionate] trihydrate

[Formula 74]

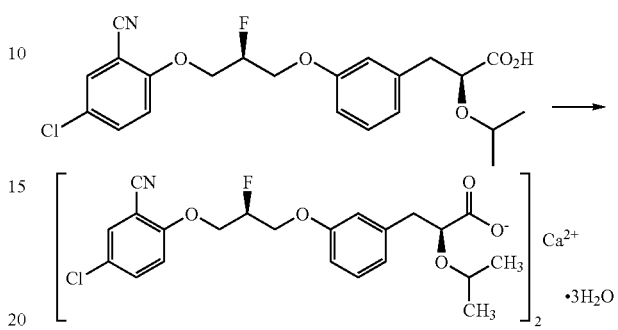

4.6 g of calcium diethoxide was dissolved in 500 mL of methanol, to which a methanol (300 mL) solution of 30.8 g of (2S)-3-[3-[(2S)-3-(4-chloro-2-cyanophenoxy)-2-fluoropropoxy]phenyl]-2-isopropoxypropionic acid was then added, followed by stirring the reaction mixture overnight at room temperature. Insoluble matter in the reaction mixture was filtered, and the solvent was distilled off under a reduced pressure. To the residue were added 250 mL of methanol and 60 mL of water, followed by heating the reaction mixture to reflux. The reaction mixture was then cooled, followed by filtering the precipitated solid to obtain 32 g of the title compound as a crude product. To this compound was added 1.5 L of ethanol, and the reaction mixture was heated to reflux. Insoluble matter was hot-filtered, and the solution was again heated to reflux. To the reaction mixture was added 20 ml of water to slowly cool the mixture, and the reaction mixture was stirred overnight at room temperature. The precipitated solid was filtered, washed with ethanol:water=9:1, and subjected to forced-air drying at 40° C. for 18 hours. There was obtained 29 g of the title compound in the form of white crystal. The $^1$H-NMR data thereof coincided with that of the compound of Example 1-(15).

Formulation Example

The compound of Example 1-(15), mannitol, corn starch, and low-substituted hydroxypropylcellulose were mixed, and then subjected to wet granulation using hydroxypropylcellulose dissolved in an appropriate amount of purified water. The granulated materials were dried and then graded, and low-substituted hydroxypropylcellulose and magnesium stearate were added to the resultant granules for mixing, followed by tableting. The amount of each raw material used per tablet is shown in the following table.

TABLE 4

| Raw material used | Intended use | 0.1 mg tablet | 1 mg tablet | 5 mg tablet |
|---|---|---|---|---|
| Compound of Example 1-(15) | Active ingredient | 0.1 | 1.0 | 5.0 |
| Mannitol | Excipient | 68.8 | 67.8 | 60.4 |
| Corn starch | Excipient | 17.0 | 17.0 | 15.1 |

TABLE 4-continued

| Raw material used | Intended use | 0.1 mg tablet | 1 mg tablet | 5 mg tablet |
|---|---|---|---|---|
| Low-substituted hydroxypropyl-cellulose | Disintegrator | 5.0 | 5.0 | 10.0 |
| Hydroxy-propyl-cellulose | Binder | 3.0 | 3.0 | 3.0 |
| Low-substituted hydroxy-propyl-cellulose | Disintegrator | 5.0 | 5.0 | 5.0 |
| Magnesium stearate | Lubricant | 1.0 | 1.2 | 1.5 |
| Purified water | Solvent | Appropriate amount | Appropriate amount | Appropriate amount |
| Total | | 100 mg | 100 mg | 100 mg |

Reference Example 1

5-chloro-2-hydroxybenzonitrile

[Formula 75]

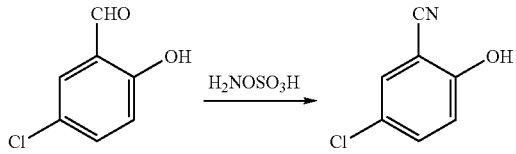

5-chloro-2-hydroxybenzaldehyde (300 g, 1.92 mol) and hydroxylamine-O-sulfonic acid (260 g, 2.30 mol) were suspended in water (4.5 L) at room temperature, which was then stirred at 60° C. for 7 hours. Water (3 L) was added to the reaction mixture, which was then cooled with ice, followed by filtering a crystal before further washing with water (1.5 L). The precipitated crystal was suspended in water (1.5 L), filtered, washed with water, and subjected to tray drying at 50° C. for 22 hours to obtain 272 g of the title compound (white crystal, yield: 93%).

$^1$H-NMR(CDCl$_3$)δ:6.94(1H, d, J=8.8 Hz), 7.42(1H, dd, J=8.8, 2.9 Hz), 7.47(1H, d, J=2.9 Hz)

INDUSTRIAL APPLICABILITY

According to the present invention, the compound of formula (I), in the form of a drug substance, is purified so as to minimize the residual solvent content and has a uniformized specification and a highly favorable workability, and a medicine containing the compound of formula (I) as an active ingredient may be therefore produced industrially.

Figure 1:
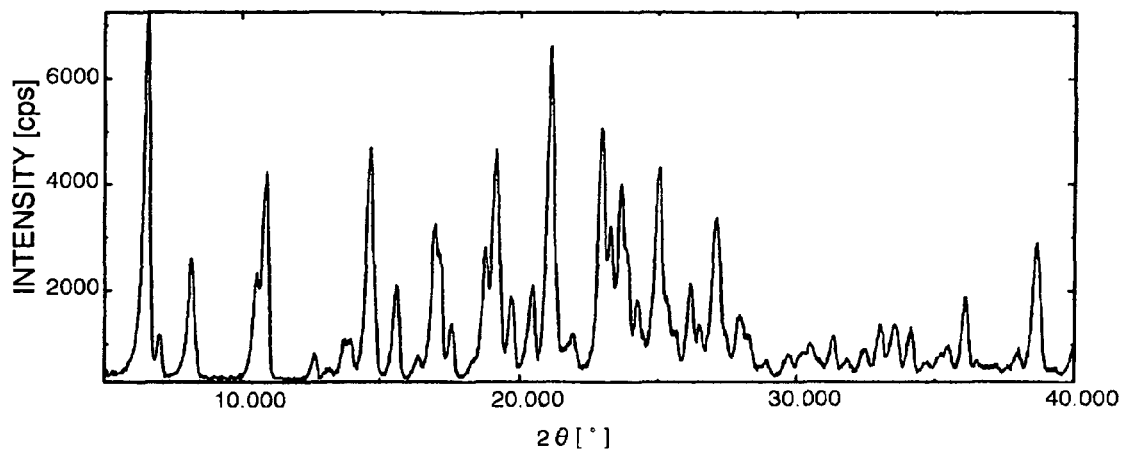
FIG. 1 is an X-ray powder diffraction pattern of the compound of formula (I-a).
Figure 2:
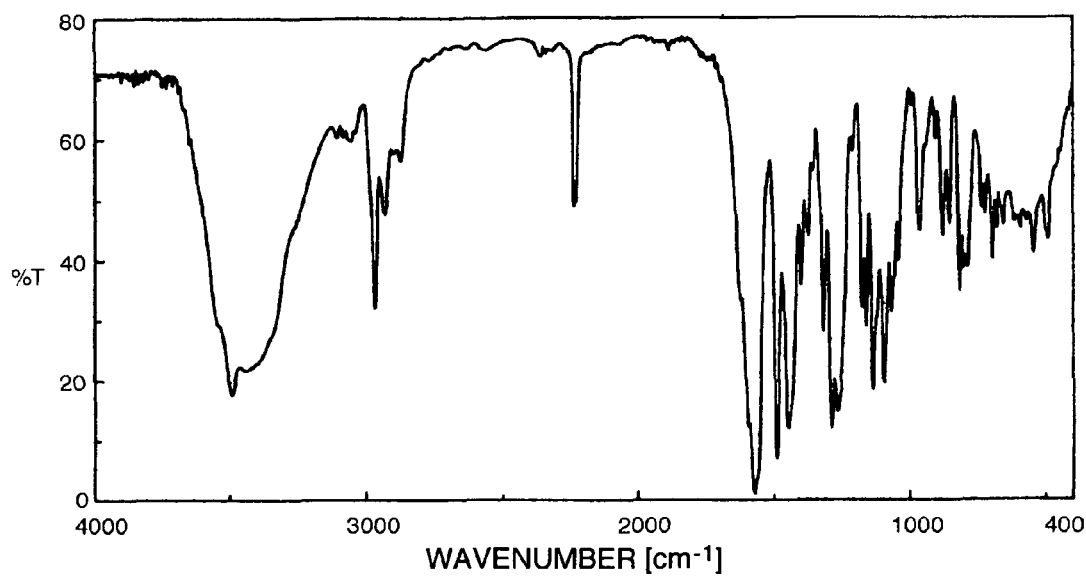
FIG. 2 is an infrared absorption spectrum of the compound of formula (I-a).
Figure 3:
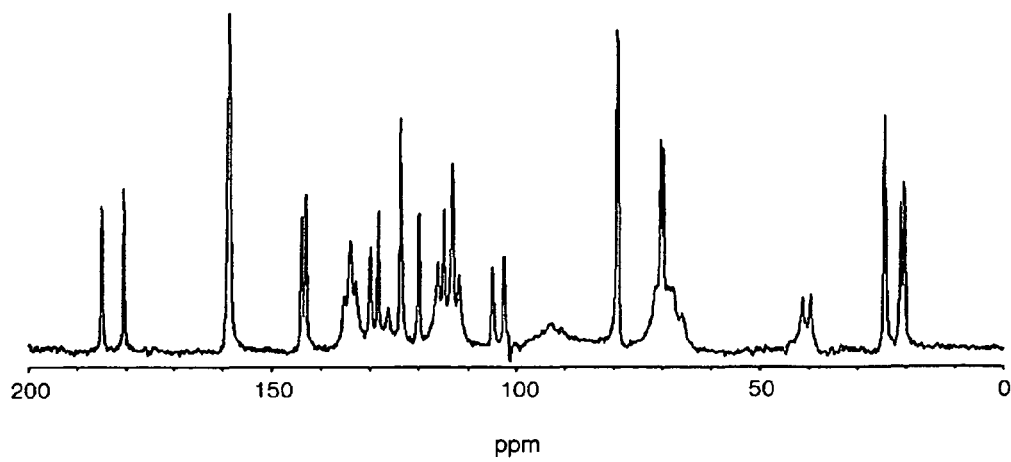
FIG. 3 is a $^{13}$C solid state NMR spectrum of the compound of formula (I-a).

The invention claimed is:

1. A crystal of calcium bis[(2S)-3-[3-[(2S)-3-(4-chloro-2-cyanophenoxy)-2-fluoropropyloxy]phenyl]-2-isopropoxypropionate] represented by formula (I-a):

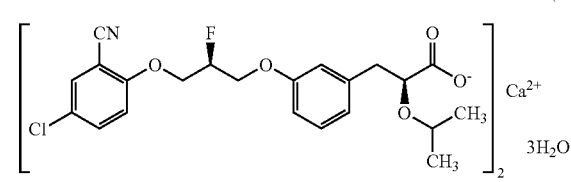

wherein the crystal of the compound has a powder X-ray diffraction pattern with peaks at diffraction angles (2 θ±0.2°) of 6.6, 8.2, 21.1, and 23.0.

2. The crystal according to claim 1, wherein the crystal has an infrared absorption spectrum with peaks at wavenumbers (±2 cm$^{-1}$) of 1573 and 2237.

3. The crystal according to claim 1, wherein the crystal has a solid state nuclear magnetic resonance spectrum with peaks at $^{13}$C chemical shifts (±1 ppm) of 185.1, 180.5, and 158.7.

4. A solid pharmaceutical composition characterized by comprising the crystal according to claim 1.

\* \* \* \* \*